United States Patent [19]

Suhadolnik et al.

[11] Patent Number: 5,556,840
[45] Date of Patent: Sep. 17, 1996

[54] 2',5'-PHOSPHOROTHIOATE OLIGOADENYLATES AS ANITIVIRAL AGENTS

[75] Inventors: Robert J. Suhadolnik, Roslyn, Pa.; Wolfgang Pfleiderer, Konstanz, Germany

[73] Assignee: Temple University - Of The Commonwealth System of Higher Education, Philadelphia, Pa.

[21] Appl. No.: 348,419

[22] Filed: Dec. 2, 1994

Related U.S. Application Data

[62] Division of Ser. No. 915,771, Jul. 16, 1992, Pat. No. 5,405,939, which is a continuation of Ser. No. 499,118, Mar. 26, 1990, abandoned, which is a continuation of Ser. No. 112,591, Oct. 22, 1987, Pat. No. 4,924,624.

[51] Int. Cl.$^6$ .......................... A61K 31/70; C07H 21/02
[52] U.S. Cl. .......................... 514/44; 514/889; 504/127; 504/129; 504/139; 504/153; 504/197; 536/25.2; 536/25.6
[58] Field of Search .......................... 514/44; 504/197; 536/25.2, 25.6

[56] References Cited

U.S. PATENT DOCUMENTS

| | | | |
|---|---|---|---|
| 4,210,746 | 7/1980 | Kerr et al. | 536/25.2 |
| 4,464,359 | 8/1984 | Suhadolnik et al. | 514/44 |
| 4,515,781 | 5/1985 | Torrence et al. | 514/47 |
| 4,565,696 | 1/1986 | Heath et al. | 424/88 |
| 4,663,161 | 5/1987 | Mannino et al. | 424/89 |
| 4,781,871 | 11/1988 | West et al. | 264/4.3 |
| 4,924,624 | 5/1990 | Suhadolnik et al. | 47/58 |
| 5,405,939 | 4/1995 | Suhadolnik et al. | 530/322 |

OTHER PUBLICATIONS

R. S. Root–Bernstein (I), "Aids Is More Than HIV: Part I," *Genetic Engineering News*, Sep. 1, 1992, pp. 4–6.
R. S. Root–Bernstein (II), "Aids Is More Than HIV: Part II," *Genetic Engineering News*, Sep. 15, 1992, pp. 4–5.
Sandstrom, "Antiviral Therapy in Human Immunodeficiency Virus Infection," *Drugs*, 38(3), 417–450 (1989); see particularly §4.4.2 (Suramin) at pp. 429–430.
Baum et al., "Aids Research Advances Steadily, But Disease Still Exacting High Toll," *Chem. Eng. News*, Am. Chem. Soc., Jun. 26, 1989, Washington, D.C., pp. 7–16.
Mitsuya et al, "Rapid In Vitro Systems for Assessing Activity of Agents Against HTLV–III/LAV," Ch. 18 in *Aids— Modern Concepts and Therapeutic Challenges*, S. Broder ed., Marcel Dekker, Inc., New York, NY, 1987, pp. 303–333.
Sharma et al., "3'-O-Methylated Analogs of 2–5A as Inhibitors of Virus Replication," *FEBS Letters*, 158(2), 298–300 (1983).
Gaswami et al., "2'–5'–Linked Oligo(adenylic Acid) and Its Analogs," *J. Biol. Chem.*, 257(12), 6867–6870 (1982).
Henderson et al., "Inhibition of Epstein–Barr Virus—Associated Nuclear Antigen (EBNA) Induction by (2'–5')–Oligoadenylate and the Cordycepin Analog: Mechanism of Action for Inhibition of EBV—Induced Transformation," *Virology*, 122, 198–201 (1982).

Eppstein et al., "Mechanism of Antiviral Activity of (XyloA2'p)$_2$XyloA," *Virology*, 131, 341–354 (1983).
"Fourth Drug to Fight HIV Infection Approved by FDA," *Chem. Eng. News*, Am. Chem. Soc., Washington, DC, 1994, p. 22, col. 1, d4T.
Zon, "Oligonucleotide Analogues as Potential Chemotherapeutic Agents," *Pharmaceutical Research*, 5(9), 539–549 (1988).
Devash et al., "Multiplication of Tobacco Mosaic Virus in Tobacco Leaf Disks is Inhibited by (2'–5') Oligoadenylate," *Science* 216, 1415–1416 (1982).
Eppstein et al., "Correlation of Structure of Analogs of ppp(A2'p)$_2$A and (A2'p)$_2$A with Stability and Biological Activity", *J. Biol. Chem.* 257 (22) 13390–13397 (1982).
Jager et al., "Synthesis of Methyl Phosphonate and Methylphosphorotriester Analogues of 2',5'–Adenylate Trimers", *Nucleic Acid Res. Symp. Series No. 9*, IRL Press Ltd., Longon, GB, pp. 149–152 (1981).
Haugh et al., "Analogues and Analogue Inhibitors of ppp(A2'p)$_n$A Their Stability and Biological Activity" *Eur. J. Biochem.* 132, 77–84 (1983).

(List continued on next page.)

*Primary Examiner*—John Kight
*Assistant Examiner*—L. Eric Crane
*Attorney, Agent, or Firm*—Seidel, Gonda, Lavorgna & Monaco, P.C.

[57] ABSTRACT

Optically active compounds of the formula

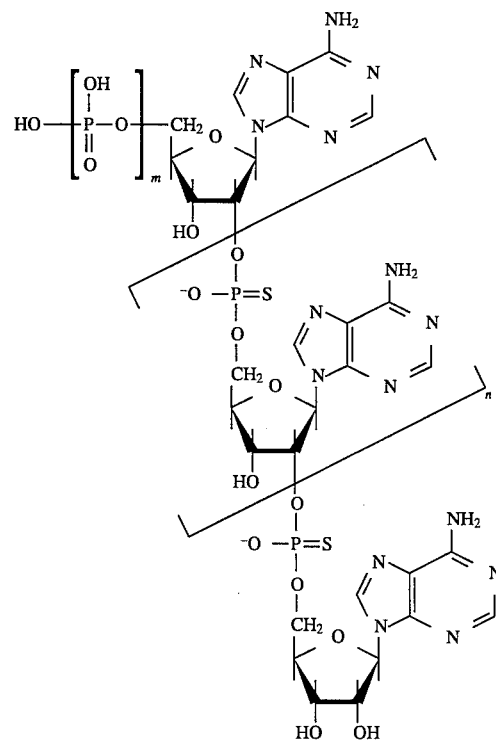

wherein n is 1 or 2 and m is 0, 1, 2 or 3 have antiviral activity. Compounds of the formula wherein at least one of the internecleotide phosphorothioate linkages is of the Sp configuration possess increased antiviral activity and/or metabolic stability.

12 Claims, 2 Drawing Sheets

OTHER PUBLICATIONS

Nelson et al., "Synthesis of P–Thioadenylyl–(2'–5')–adenosine and P–Thioadenylyl–(2'–5')–P–thioadenylyl–(2'–5')–thioadenylyl–(2'–5')–adenosine", *J. Org. Chem.*, 49, 2314–2317 (1984).

Eppstein et al., "Stereochemical Configuration Markedly Affects the Biochemical and Biological Properties of Phosphorothioate Analogs of 2–5A Core, (A2'p5')$_2$A", *J. Biol. Chem.* 261, 5999–6003 (1986); correction at *J. Biol. Chem.* 261(29) 13873 (1986).

Lee et al., "2',5'-Oligoadenylates Chiral at Phosphrus: Enzymatic Synthesis, Properties, and Biological Activity or 2',5'-Phosphorothioate Trimer and Tetramer Analogues Synthesized from (S$_p$)-ATPαS", *Biochemistry* 24(3), 551–555 (1985).

Lee et al. (11), "Chiral and Achiral Phosphorothioate Analogs of 2',5'-Oligo(A): Enzymatic Synthesis, Purification and Biological Properties," *Fed. Proceedings,* 44(5), 1802 (1985) see abstract No. 8126.

Suhadolnik et al., "Chiral and Achiral Phosphorothioate Analogs of 2–5A: Enzymatic Synthesis Characterization and Biological Activities," in *The 2–5A System: Molecular and Clinical Aspects of the Interferon—Regulated Pathway*, published by Alan R. Liss, Inc., pp. 115–122 (1985).

Pauwels et al., "Biological Activity of New 2–5A Analogs," *Chem. Scr.* 26(1) 141–145 *Chem. Abstr.* 105, Abstr. No. 151228t; only Abstr. supplied.

Schryver et al., "2–5A Analogs as Mechanistic Probes of the 2–5A System: Stereoconfiguration of Phosphorothioate Analogs of 2–5A Markedly Influences Metabolic Stability," in *The 2–5A System: Molecular and Clinical Aspects of the Interferon—Regulated Pathway*, published by Alan R. Liss, Inc., plp. 81–88 (1985).

Bayard et al., "Activation of Ribonuclease L by (2'–5')(A)4–Poly(L–Lysine) Conjugates in Intact Cells", *Biochemistry,* 26(12), 3730–3736 (1986).

Kariko et al., "Phosphorothioate Analogs of 2–5A. Activation of RNASE L by Trimer Cores and 5'-Monophosphates", *Federation Proc.* 46(6), Abstr. 922 (1987).

Kariko et al., "Phosphorothioate Analogs of 2–5A: Elucidation of the Stereochemical Course of the Enzymes of the 2–5A Synthetase/RNASE L System", *Nucleosides & Nucleotides* 6 (1&2), 173–184 (1987).

Lehniger, *Biochemistry, Second Edition,* Worth Publishers, Inc., New York, NY p. 315 (1978).

2',5'-PHOSPHOROTHIOATE OLIGOADENYLATES AS ANITIVIRAL AGENTS

This is a divisional of application Ser. No. 07/915,771, filed Jul. 16, 1992, now U.S. Pat. No. 5,405,939, which is a continuation of application Ser. No. 07/499,118, filed Mar. 26, 1990, now abandoned, which is a continuation of application Ser. No. 07/112,591 filed Oct. 22, 1987, U.S. Pat. No. 4,924,624.

FIELD OF THE INVENTION

The invention relates to synthetic analogues of naturally occurring antiviral 2',5'-oligoadenylates wherein the internucleotide phosphodiester linkages are replaced with optically active phosphorothioate groups. The compounds have increased metabolic stability where the stereoconfiguration around one or more of the chiral phosphorous atoms is the Sp configuration.

REFERENCE TO GOVERNMENT GRANT

The invention described herein was made, in part, in the course of work supported by National Institutes of Health grant PO1 CA-29545 and National Science Foundation grant DMB84-15002.

BACKGROUND OF THE INVENTION

The full nomenclature of the subject matter of the present invention involves extremely long terms. It is customary for those skilled in the art to abbreviate oligoadenylate analogues and related terms in a manner well-known to them. These general and customary abbreviations are set forth herein below and may be utilized in the text of this specification.

Abbreviations:

2-5A, 2',5'-oligoadenylate or $p_3A_n$: Oligomer of adenylic acid with 2',5'-phosphodiester linkages and a 5'-terminal triphosphate group.

$A_2$, $A_3$ and $A_4$: Dimer, trimer and tetramer of adenylic acid with 2',5'-phosphodiester linkages.

$pA_3$, $ppA_3$ (or $p_2A_3$), $pppA_3$ (or $p_3A_3$): 5'-terminal mono-, di- and triphosphates of $A_3$.

AMPS: Adenosine 5'-O-phosphorothioate.

SVPD: Snake venom phosphodiesterase.

2'-PDE: 2'-phosphodiesterase

Rp: The R stereoconfiguration about a chiral phosphorous atom in a phosphorothioate internucleotide linkage.

Sp: The S stereoconfiguration about a chiral phosphorous atom in a phosphorothioate internucleotide linkage.

RNase L: 2-5A dependent endoribonuclease.

$A_{Rp}A_{Rp}A$: (Rp)-P-thioadenylyl-(2'-5')- (Rp)-P- thioadenylyl-(2'-5')-adenosine.

$A_{Sp}A_{Rp}A$: (Sp)-P-thioadenylyl-(2'-5')- (Rp)-P- thioadenylyl-(2'-5')-adenosine.

$A_{Rp}A_{Sp}A$: (Rp)-P-thioadenylyl-(2'-5')- (Sp)-P- thioadenylyl-(2'-5')-adenosine.

$A_{Sp}A_{Sp}A$: (Sp)-P-thioadenylyl-(2'-5')- (Sp)-P- thioadenylyl-(2'-5')-adenosine.

$pA_{Rp}A_{Rp}A$, $ppA_{Rp}A_{Rp}A$, $pppA_{Rp}A_{Rp}A$, $pA_{Sp}A_{Rp}A$, $ppA_{Sp}A_{Rp}A$, $pppA_{Sp}A_{Rp}A$, $pA_{Rp}A_{Sp}A$, $ppA_{Rp}A_{Sp}A$, $pppA_{Rp}A_{Sp}A$, $pA_{Sp}A_{Sp}A$, $ppA_{Sp}A_{Sp}A$, and $pppA_{Sp}A_{Sp}A$: 5'-mono-, di- and triphosphates of $A_{Rp}A_{Rp}A$, $A_{Sp}A_{Rp}A$, $A_{Rp}A_{Sp}A$ and $A_{Sp}A_{Sp}A$.

$A_{Rp}A_{Rp}A_{Rp}A$: (Rp)-P-thioadenylyl-(2'-5')-(Rp)-P- thioadenylyl-(2'-5')-(Rp)-P-thioadenylyl-(2'-5')-adenosine.

$A_{Rp}A_{Sp}A_{Rp}A$: (Rp)-P-thioadenylyl-(2'-5')-(Sp)-P- thioadenylyl-(2'-5')-(Rp)-P-thioadenylyl-(2'-5')-adenosine.

$A_{Rp}A_{Rp}A_{Sp}A$: (Rp)-P-thioadenylyl-(2'-5')-(Rp)-P- thioadenylyl-(2'-5')-(Sp)-P-thioadenylyl-(2'-5')-adenosine.

$A_{Rp}A_{Sp}A_{Sp}A$: (Rp)-P-thioadenylyl-(2'-5')-(Sp)-P- thioadenylyl-(2'-5')-(Sp)-P-thioadenylyl-(2'-5')-adenosine.

$A_{Sp}A_{Rp}A_{Rp}A$: (Sp)-P-thioadenylyl-(2'-5')-(Rp)-P -thioadenylyl-(2'-5')-(Rp)-P-thioadenylyl-(2'-5')-adenosine.

$A_{Sp}A_{Sp}A_{Rp}A$: (Sp)-P-thioadenylyl-(2'-5')-(Sp)-P- thioadenylyl-(2'-5')-($R_p$)-P-thioadenylyl-(2'-5')-adenosine.

$A_{Sp}A_{Rp}A_{Sp}A$: (Sp)-P-thioadenylyl-(2'-5')-(Rp)-P- thioadenylyl-(2'-5')-(Sp)-P-thioadenylyl-(2'-5')-adenosine.

$A_{Sp}A_{Sp}A_{Sp}A$: (Sp)-P-thioadenylyl-(2'-5')-(Sp)-P- thioadenylyl-(2'-5')-(Sp)-P-thioadenylyl-(2'-5')-adenosine.

$pA_{Rp}A_{Rp}A_{Rp}A$, $ppA_{Rp}A_{Rp}A_{Rp}A$, $pppA_{Rp}A_{Rp}A_{Rp}A$, $pA_{Rp}pA_{Sp}A_{Rp}A$, $ppA_{Rp}A_{Sp}A_{Rp}A$, $pppA_{Rp}A_{Sp}A_{Rp}A$, $pA_{Rp}A_{Rp}pA_{Sp}A$, $ppA_{Rp}A_{Rp}A_{Sp}A$, $pppA_{Rp}A_{Rp}A_{Sp}A$, $pA_{Rp}A_{Sp}A_{Sp}A$, $ppA_{Rp}A_{Sp}A_{Sp}A$, $pppA_{Rp}A_{Sp}A_{Sp}A$, $pA_{Sp}A_{Rp}A_{Rp}A$, $ppA_{Sp}A_{Rp}A_{Rp}A$, $pppA_{Sp}A_{Rp}A_{Rp}A$, $pA_{Sp}A_{Sp}A_{Rp}A$, $ppA_{Sp}A_{Sp}A_{Rp}A$, $pppA_{Sp}A_{Sp}A_{Rp}A$, $pA_{Sp}A_{Rp}A_{Sp}A$, $ppA_{Sp}A_{Rp}A_{Sp}A$, $pppA_{Sp}A_{Rp}A_{Sp}A$, $pA_{Sp}A_{Sp}A_{Sp}A$, $ppA_{Sp}A_{Sp}A_{Sp}A$, $pppA_{Sp}A_{Sp}A_{Sp}A$: 5'-mono-, di- and triphosphates of the above tetramers.

(Sp)-ATP-alpha-S: Adenosine 5'-O-(Sp)-(1- thiotriphosphate).

BACKGROUND OF THE INVENTION

The 2-5A system is widely expected to be involved in the antiviral mechanism of interferon and may also be involved in the regulation of cell growth and differentiation. 2-5A synthesized from ATP by 2',5'-oligoadenylate synthetase [ATP: (2'-5')oligo(A)-adenyltransferase (EC 2.7.7.19)] exerts its biological effects by binding to and activating its only known target enzyme, the unique 2-5A-dependent endoribonuclease RNase L (EC 3.1.27). RNase L cleaves vital and cellular mRNA or rRNA, thereby inhibiting protein synthesis. Hovanessian et al, *Eur. J. Biochem.* 93:515–526 (1979); Kerr et al, *Proc. Natl. Acad. Sci. USA.* 75:256–260 (1978). It has been reported that 2-5A protects plant tissue from infection by tobacco mosaic virus. Devash et al, *Science* 216:415 (1982). 2-5A, however, is metabolically unstable. It is degraded by a cellular 2'-phosphodiesterase and phosphatases. Knight et al, *Meth. Enzymol.* 79: 216–227 (1981); Minks et al, *Nucleic Acids Res.* 6:767–780 (1979); Williams et al, *Eur. J. Biochem.* 92:455–462 (1978).

The literature is replete with structurally-modified 2-5A molecules with modifications in the adenyl or ribosyl moiety designed to explore the biological role of the 2-5A synthetase/RNase L system. The primary source of conformational flexibility in the 2-5A molecule is in the backbone, similar to 3',5'-linked RNA and DNA. Srinivasan et al, *Nucleic Acids Res.* 13:5707–5716 (1985). However, theoretical and experimental analyses have revealed that the conformation of 2',5'-linked dinucleotides and polynucleotide chains are significantly different from 3',5'-linked nucleotides. Id. The ribose-phosphate backbone of 2-5A has also been demonstrated to be the major antigenic determinant in the molecule. Johnston et al, *Biochemistry* 22:3453–3460 (1983).

Few reports have appeared on the synthesis of 2-5A analogues with backbone modifications. Core analogues containing methylphosphonate and methylphosphotriester groups have been synthesized. Eppstein et al, *J. Biol. Chem.* 257:13390–13397 (1982); Jager et al, *Nucleic Acids Res. Sym. Ser. No.* 9:149–152 (1981). However, complete loss of activity was observed with the "uncharged" methylphosphotriester analogues. Eppstein et al, supra. Substitution of the 2',5'-phosphodiester linkages with 3', 5'-linkages has also lead to substantial decrease in biological activity. Lesiak et al, *J. Biol. Chem.* 258:13082–13088 (1983). Replacement of only one 2',5'-internucleotide linkage has resulted in at least one order of magnitude loss of activity. Nearly complete loss of biological activity was observed when both 2',5'-phosphodiester linkages in the 2-5A trimer were replaced with 3',5'-bonds.

Haugh et al, *Eur. J. Biochem.* 132:77–84 (1983), reported that the affinity of $pA_3$ to RNase L in mouse L929 cell extracts is approximately 1,000 times greater than that of $A_3$.

Nelson et al, *J. Org. Chem.* 49:2314–2317 (1984), describe diastereomeric pairs of the phosphorothioate analogue of $A_3$ without resolution of individual enantiomers. Eppstein et al, *J. Biol. Chem.* 261:5999–6003 (1986) report metabolic stabilities and antiviral activity of purported $A_{Rp}A_{Rp}A/A_{Sp}A_{Rp}A$ and $A_{Rp}A_{Sp}A/A_{Sp}A_{Sp}A$ racemic mixtures without resolution of individual enantiomers.

Lee and Suhadolnik, *Biochemistry* 24:551–555 (1985), and Suhadolnik and Lee in *The 2-5A System: Molecular and Clinical Aspects of the Interferon-Regulator Pathway*, Williams, B. R. G. and Silverman, R. H., Eds. (1985), Alan R. Liss, Inc., New York, p. 115–122, disclose the enzymatic synthesis of the alpha-phosphorothioate 5'-triphosphates of $A_{Rp}A_{Rp}A$ and $A_{Rp}A_{Rp}A_{Rp}A$ from (Sp)-ATP-alpha-S. Such compounds are metabolically unstable. Preparation of the corresponding stereoisomers with Sp internucleotide phosphorothioate linkages was not possible owing to the stereospecificity of 2-5A synthetase for the substrate (Sp)-ATP-alpha-S, which is inverted to yield trimer and tetramer products containing 2',5'-phosphorothioate internucleotide linkages of the Rp configuration exclusively. Because nucleoside tranferases provide exclusively the inverted configuration when Sp-ATP-alpha-S is the substrate, 2',5'-phosphorothioate oligoadenylates containing internucleotide phosphorothioate groups of the Sp configuration cannot be synthesized enzymatically.

SUMMARY OF THE INVENTION

Compounds of the present invention useful in inhibiting vital infections in plants and in mammals have increased metabolic stability and/or antiviral activity.

The compounds are optical isomers and water-soluble salts thereof of the formula

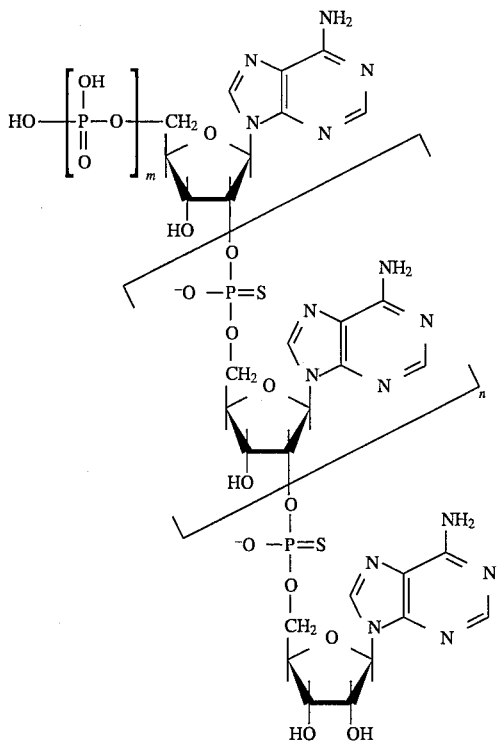

substantially free of contamination by other optical isomers of the same formula, wherein m is zero, 1,2 or 3; n is 1 or 2; and at least one of the internucleotide phosphorothioate groups

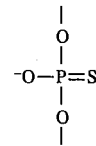

is of the Sp configuration.

The invention also comprises a method of inhibiting viral infection in mammals or plants by administering an antiviral effective amount of a compound according to the above formula, or a water-soluble salt thereof, and antiviral compositions containing such compounds with a carrier.

Compounds according to the formula wherein n is 2 may be utilized to form oligoadenylate conjugates with the macromolecular carrier poly(L-lysine) for intracellular transport Such poly(L-lysine)/2',5'-phosphorothioate oligoadenylate conjugates have the formula

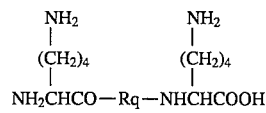

wherein q is an integer from about 60 to about 70, and R is randomly R' or

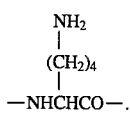

From about five to about ten of the R groups comprise R'. R' has the following formula wherein m is 0,1,2 or 3:

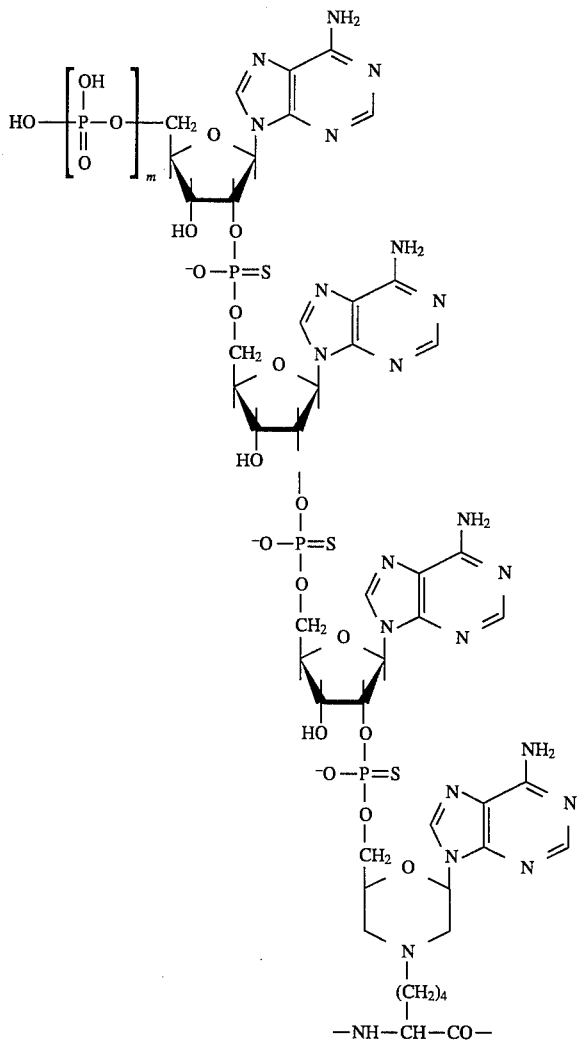

Preferably, at least one of the phosphorothioate groups

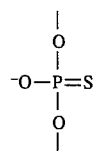

of the poly(L-lysine)/2',5'-phosphorothioate oligoadenylate conjugates is of the Sp configuration.

DETAILED DESCRIPTION OF THE INVENTION

Figure 1A:
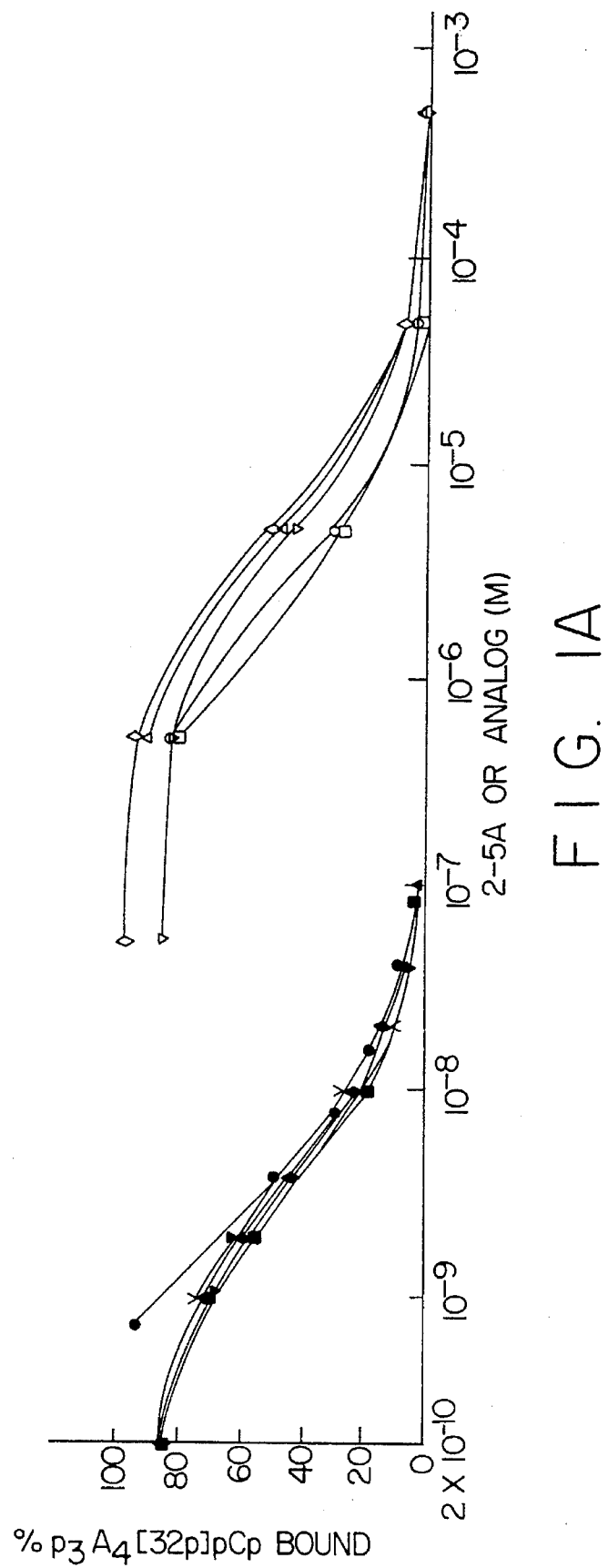
FIG. 1A represents the results of a radiobinding assay indicating the ability of 2',5'-phosphorothioate adenylate trimer cores and 5'-monophosphates to compete with $p_3A_4$ [$^{32}$P]pCp for binding to the RNase L in L929 cell extracts. Approximately 60% of the probe was bound in the absence of added oligonucleotide (total dpm=23,000). The curves are labelled as follows: $A_3$ (o); $p_3A_3$ (×); $pA_3$ (●); $A_{Rp}A_{Rp}A$ (∇); $A_{Sp}A_{Rp}A$ (◊); $A_{Rp}A_{Sp}A$ (△); $A_{Sp}A_{Sp}A$ (□); $pA_{Rp}A_{Rp}A$ (▼); $pA_{Sp}A_{Rp}A$ (♦); $pA_{Rp}A_{Sp}A$ (▲); $pA_{Sp}A_{Sp}A$ (■).

The activation of the unique 2-5A-dependent endoribonuclease, RNase L, by 2',5'-oligoadenylates, and its hydrolysis of rRNA, tRNA and cellular and vital mRNA, is important in the inhibition of vital replication and regulation of cell growth. RNase L is known to be the substrate target for 2-5A. It is one of the chief functional enzymes of the interferon-induced biological cascade. While modified analogues of 2-5A have been reported, they are not metabolically stable, or fail to activate RNase L. The introduction of the phosphorothioate group in the 2',5'-internucleotide linkages of 2-5A, induces physical, chemical and biochemical modifications in the 2-5A molecule including (i) Rp/Sp chirality, (ii) lowered pKa, (iii) altered metal ion chelation, (iv) charge modulation, (v) increased bond length, (vi) altered degree of hydration and (vii) increased metabolic stabilities.

The metabolic stability of the 2',5'-phosphorothioate oligoadenylates is greater than authentic 2-5A. This metabolic stability is greatly enhanced where at least one of the internucleotide phosphorothioate 2',5'-linkages is of the Sp configuration. While racemic mixtures of the trimer cores have been reported, Nelson et al, *J. Org. Chem.* 49:2314–2317 (1984) and Eppstein et al, *J. Biol. Chem* 261:5999–6003 (1986), efforts to resolve the compounds have failed. The level of antiviral activity of the trimer core racemates reported by Eppstein et al is such that the dosages required for treatment would be prohibitively toxic. At least one of the purported racemates of Eppstein et al, the $A_{Rp}A_{Sp}A/A_{Sp}A_{Sp}A$ racemate, is of little value since, as we have found, the $A_{Sp}A_{Sp}A$ stereoisomer selectively inactivates RNase L, thereby preventing $A_{Rp}A_{Sp}A$ from exerting its antiviral effect through activation of RNase L. This is most undesirable since, as we have found, $A_{Rp}A_{Sp}A$ is the most attractive of the four trimer core stereoisomers, since it both activates RNase L and is metabolicly stable.

We have succeeded in preparing the fully resolved 2',5'-phosphorothioate adenylate trimer cores, thus making possible the practical use of the important $A_{Rp}A_{Sp}A$ stereoisomer. Our method of stereo-specific chemical synthesis also makes possible the preparation of the eight separate stereoisomers of the 2',5'-phosphorothioate tetramer. Preparation of the tetramer molecules enables conjugation with the carrier (poly)L-lysine, shown to be an effective vector for introducing 2',5'-oligoadenylates and analogues into intact cells. Poly(L-lysine) conjugation to trimer molecules is not feasible, owing to the destruction of the 2'-terminal ribosyl moiety and subsequent inactivation of the molecule. Conjugation to poly(L-lysine) permits efficient intracellular transport of the 2',5'-phosphorothioate oligoadenylates while preserving intact within the conjugate the trimer moiety believed necessary for good biological activity.

Correlation of biological properties with absolute configuration has only been possible with the preparation of the fully resolved 2',5'-phosphorothioate adenylate trimer cores described herein. However, the trimer core compounds have been found to bind and/or activate RNase L only modestly. We have found that the RNase L activation by the 2',5'-phosphorothioate core molecules is significantly enhanced by 5'-phosphorylation.

PNase L activation by authentic 2-5A requires the triphosphate form of the trimer. The 5'-monophosphate form of 2-5A is a potent inhibitor of the RNase L-activating activity of the triphosphate. Miyamoto et al., *J. Biol. Chem* 258: 15232–15237 (1983); Black et al., *FEBS Let.* 191:154–158 (1985); Torrence et al., *Proc. Natl. Acad. Sci. USA* 78:5993–5997 (1981). We have surprisingly found that the cores and monophosphates of the present phosphorothioate analogues of 2-5A, unlike authentic 2-5A, activate RNase L.

The phosphorothioate trimer cores $A_{Rp}A_{Rp}A$, $A_{Sp}A_{Rp}A$, $A_{Rp}A_{Sp}A$, and $A_{Sp}A_{Sp}A$, are chemically synthesized and separated by preparative thin layer chromatography on silica gel. The four trimer cores are prepared from 6-N-benzoyl-3'-O-tert-butyldimethylsilyl-5'-O-monomethoxytrityladenosine-2-O-(p-nitrophenylethyl)-octahydroazonino-phosphoramidite by stereospecific synthesis, which relies on separation of fully resolved protected intermediates followed by removal of all blocking groups to yield the fully-resolved 2',5'-phosphorothioate trimer adenylate cores.

The trimer cores are prepared according to the following reaction scheme wherein "BZ" denotes the benzoyl radical "Si" denotes the tert-butyldimethylsilyl radical and "MMTr" represents the monomethoxytrityl radical. While not part of the invention, the preparation of the dimer core enantiomers $A_{Rp}A$ (6A) and $A_{Sp}A$ (6B) is included for completeness.

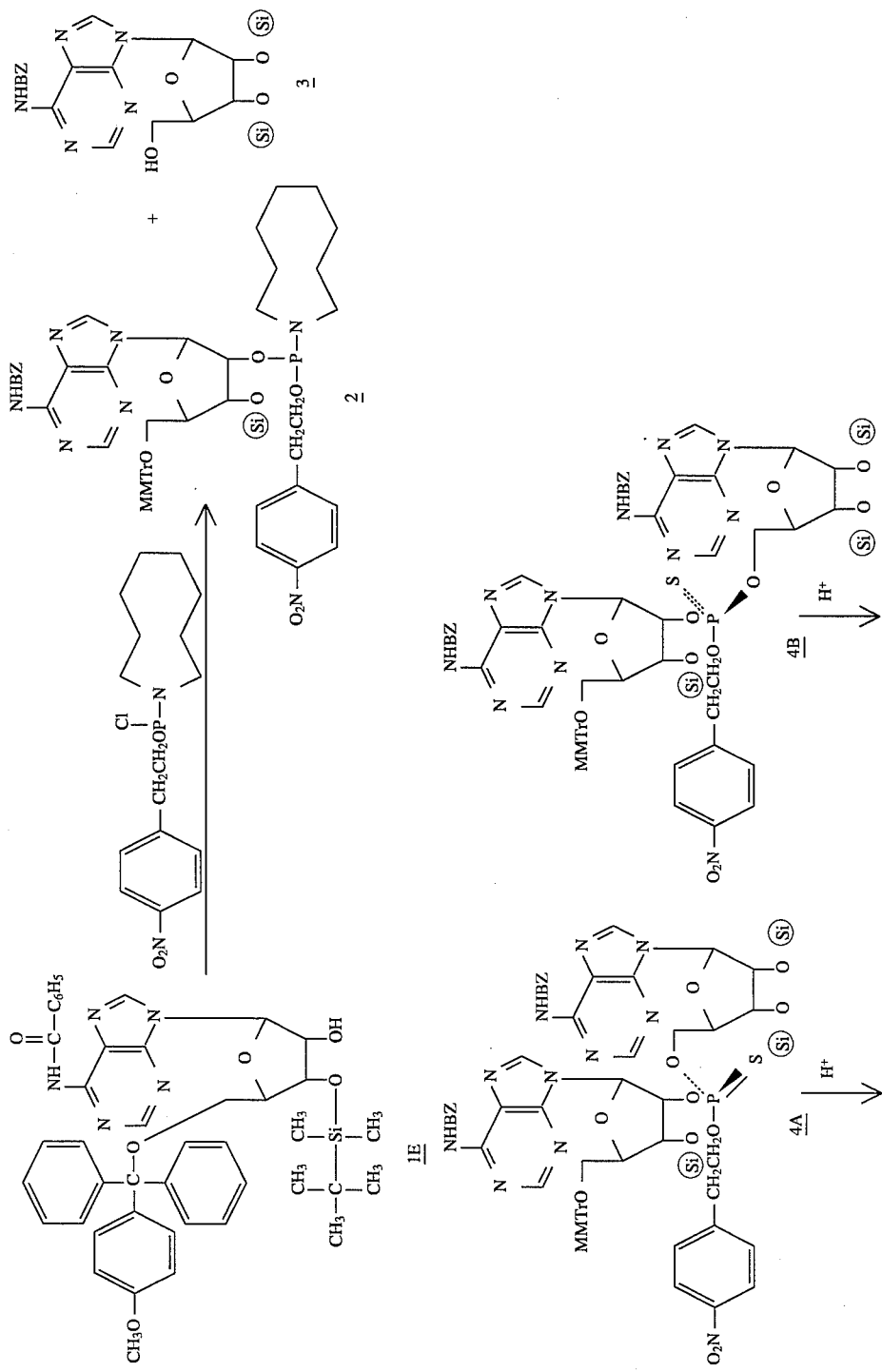

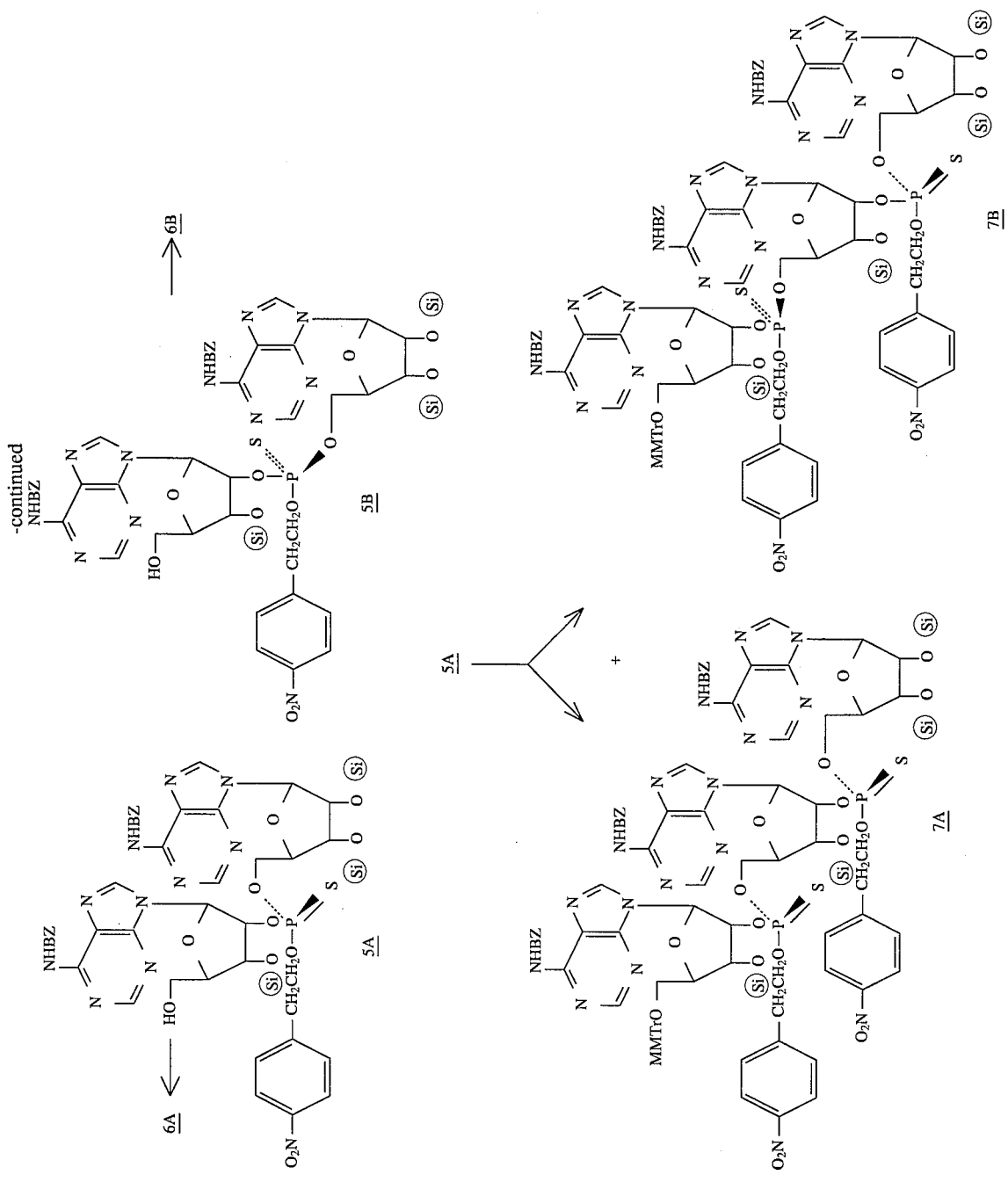

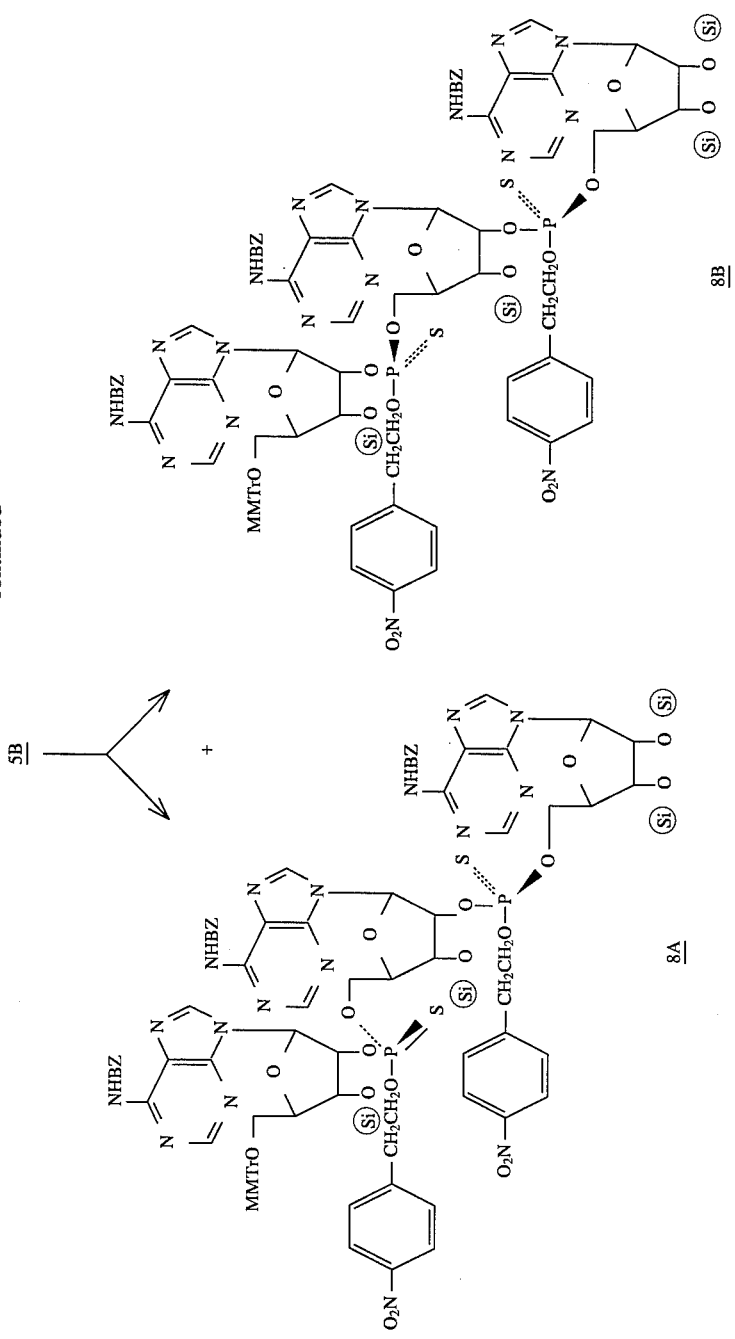

The blocking groups are removed from the fully-protected intermediates 7A, 7B, 8A, and 8B to yield the corresponding fully resolved trimer cores $A_{Rp}A_{Rp}A$ (9A), $A_{Sp}A_{Rp}A$ (9B), $A_{Rp}A_{Sp}A$ (10A) and $A_{Sp}A_{Sp}A$ (10B):

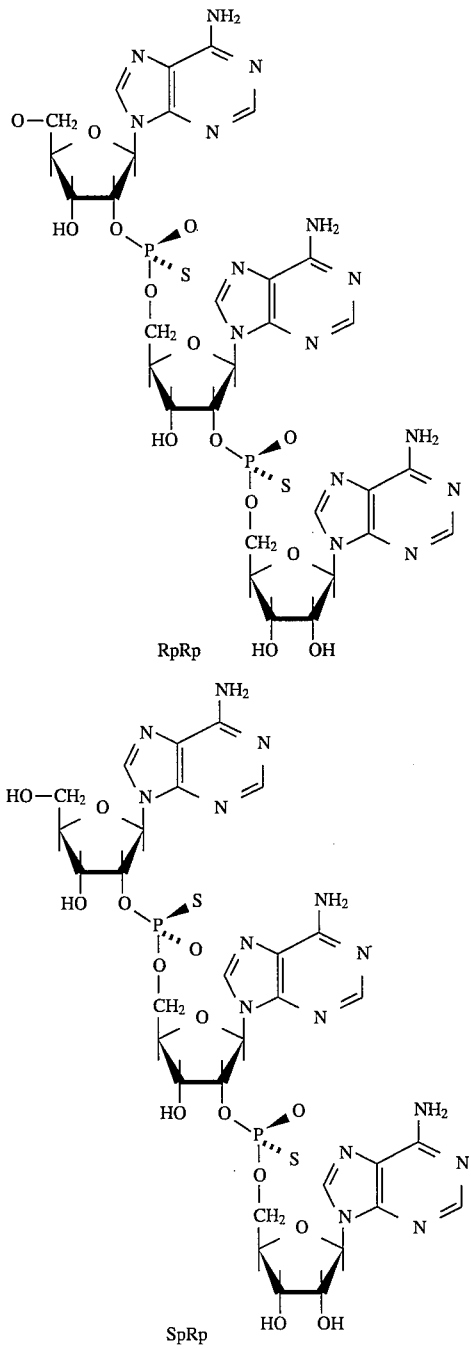

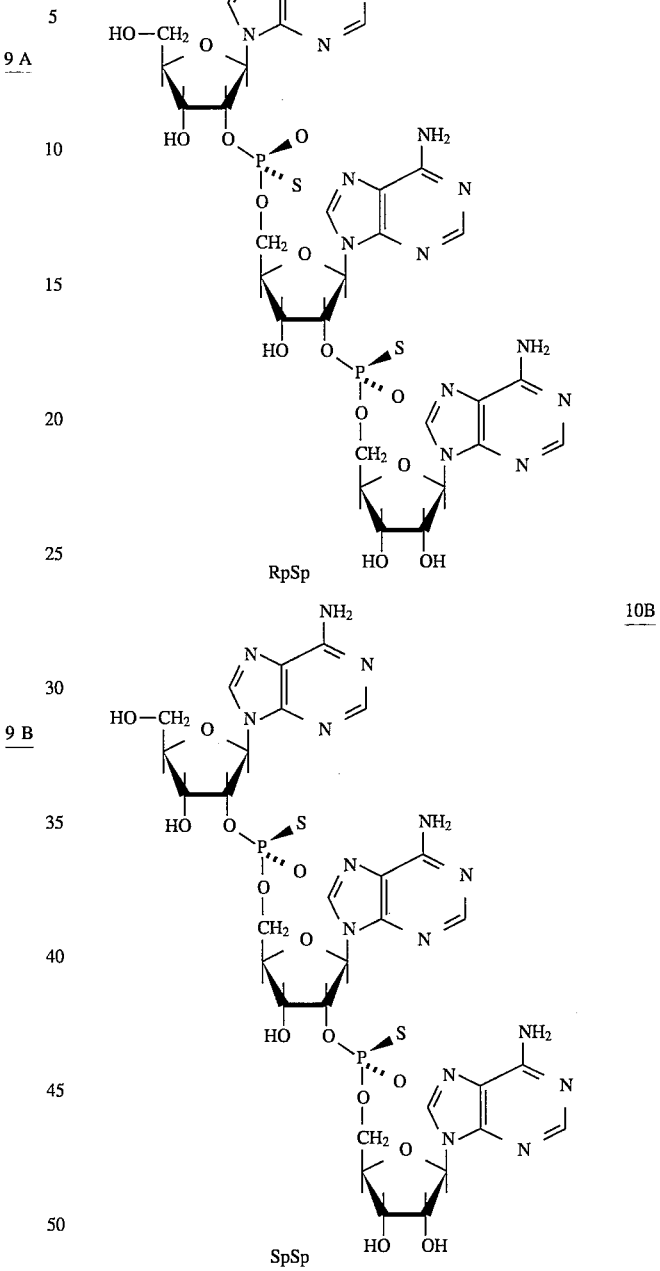

The compounds of the invention are advantageously prepared as soluble salts of sodium, ammonium or potassium. The preparative scheme begins with 6-N-benzoyl-3'-O-tert-butyldimethylsilyl- 5'-O-monomethoxy-trityladenosine (compound 1E), which is advantageously prepared from adenosine according to the procedure of Flockerzi et al, *Liebigs Ann. Chem.*, 1568–1585 (1981).

Preparation of the compounds of the present invention is illustrated in more detail by reference to the following non-limiting examples. 3-Nitro-1,2,4-triazole; chlorooctahydroazonino-p-nitrophenylethoxyphosphate; 2,5-dichlorophenylphosphoro-dichloridate; and p-nitrophenylethanol used in the examples may be prepared advantageously from published procedures: Chattopadhyaya et. al. *Nucleic Acids Res.* 8:2039–2053 (1980); Schwarz et al., *Tetrahedron Lett.* 5513–5516 (1984); Uhlmann et al., *Helv. Chim. Acta* 64:1688–1703 (1981). These compounds are also available commercially in the United States. 2,5 -Dichlorophenylphosphorodichloridate may be obtained from Fluka Chemical Corp., 980 S. Second St., Ronkonkoma, N.Y. 11779, ("Catalog 15: Chemika-Biochemika" 1986/1987, no. 36212). 3-Nitro-1,2,4-triazole is available from Aldrich Chemical Co., P.O. Box 355, Milwaukee, Wis. 53201 (1986-1987 cat. no. 24,179.2). P-Nitrophenylethanol is available from Fluka Chemical Corp. (cat. no. 73,610). Chloro-octahydroazonino-p-nitrophenylethoxyphosphate may be prepared according to Example 1A, below.

Pyridine and triethylamine used in the examples were purified by distillation over KOH, tosyl chloride and calcium hydride. Dichloromethane was distilled over calcium chloride and then passed through basic alumina. Pure acetonitrile was obtained by distillation over calcium hydride.

Purification of the protected nucleotides was achieved by preparative column chromatography on silica gel 60 (0.063–0.2 mesh, Merck) and by preparative thick layer chromatography on silica gel 60 PF$_{254}$ (Merck). Thin layer chromatography ("TLC") was carried out on precoated thin layer sheets F 1500 LS 254 and cellulose thin layer sheets F 1440 from Schleicher & Scheull.

The starting material, 6-N-Benzoyl-3-O-tert-butyldimethylsilyl- 5'-O-(4-monomethoxytrityl)adenosine (Compound 1E) and the reagent 6-N-benzoyl-2',3'-bis-O-(tert-butyldimethylsilyl)-adenosine (Compound 1G), are prepared according to Example 1.

EXAMPLE 1 a N$^6$,N$^6$,2',3',5'-O-Pentabenzoyladenosine:

(1A) To a suspension of 5.34 g (20 mmole) adenosine (Sigma, dried at 80° C./10$^{-3}$ Torr for 24 h) in 100 ml dry pyridine, 33.74 g (240 mmole) benzoyl chloride was added dropwise. After 20 h stirring at room temperature ("r.t.") the mixture was treated with 16 ml dry MeOH and then extracted with CHCl$_3$ (3×250 ml). The organic phase was washed with water (3×250 ml), dried over Na$_2$SO$_4$, and evaporated to dryness. Final coevaporation was performed with toluene. The residue was dissolved in CHCl$_3$/MeOH 2/1 by heating, and after cooling to r.t., petrolether (diethylether) was added until the solution became turbid. After standing for 12 h at 0° C. 12.18 g was obtained, and from the mother liquor, 2.66 g of the product were isolated as colorless needles of m.p. 183°–184° C., yield 14.84 g (94%).

b. 6-N-Benzoyl adenosine (1B):

A solution of 7.88 g (10 mmole) of the pentabenzoyl adenosine (1A) in 150 ml dry pyridine and 50 ml dry MeOH was treated with 50 ml 1M sodium methylate solution. After 15 min the solution was poured onto an ice cold solution of a 110 ml DOWEX ion exchanger 50×4 (pyridinium form) in ca 20 ml water. After 5 h stirring the pH was 5.5–6.0. After filtering from the ion exchanger, the residue was washed with boiling MeOH/water (3/1). The filtrate was evaporated to dryness and crystallized from MeOH/water 2/1 to give 3.25 g (83%) of the product as colorless needles, m.p. 151°–153° C.

c. 6-N-Benzoyl-5'-O-(4-methoxytrityl) adenosine (1C):

17.9 g (46 mmole) 6-N-benzoyl adenosine.H$_2$O (1B) was evaporated with dry pyridine (3×100 ml) and finally dissolved in 150 ml dry pyridine and 21.31 g (69 mmole) p-monomethoxytrityl chloride. The reaction solution was stirred at 50° C. for 14 h and dry MeOH (50 ml) was added and allowed to come to r.t. The product was extracted with CHCl$_3$ (3×400 ml) and washed with water (3×400 ml). The organic phase was dried over Na$_2$SO$_4$ and evaporated to dryness. Final coevaporation was performed with toluene. Purification was performed using a silica gel column (16× 2.5 cm, Merck) and eluted with 3 liter EtOAc/MeOH 7/3 to give 25.6 g (87%) of an amorphous powder. Crystallization was accomplished with acetone/water to yield the product, m.p. 120°–125° C.

d.  6-N-Benzoyl-2'-O-(tert-butyldimethylsilyl)-5'-O-(4-methoxytrityl) adenosine (1D);
6-N-Benzoyl-3'-O-(tert-butyldimethylsilyl)-5'-O-(4 -methoxytrityl) adenosine (1E);
6-N-benzoyl-2',3'-O-bis(tert-butyldimethylsilyl)-5'-O-(4-methoxytrityl) adenosine (1F):

To a solution of 4.05 g (26.9 mmole) tert-butyldimethylsilylchloride ("TBDMS-Cl") and 3.66 g (53.8 mmole) imidazole in 100 ml dry pyridine, were added 14.42 g (22.4 mmole) of compound 1C which was previously coevaporated with dry pyridine. After 15 h stirring at r.t., 5 ml dry MeOH was added and the mixture was evaporated to ⅓ volume. The crude product was extracted with CHCl$_3$ (3×250 ml) and washed with water. Upon evaporation, the crude product was first purified by a silicagel column (15×3 cm) with CH$_2$Cl$_2$/EtOAc (9/1), and subsequently purified using medium pressure chromatography (silicagel column, GSF-type C (N=9000, V$_D$=28 ml) at 8–10 bar pressure with the following mixtures of CH$_2$Cl$_2$/petrolether/EtOAc/EtOH: 100:100:10:0.5 (2 liters, first; 100/100/10/1 (3 liters), second; and 100/100/31/2 (0.5 liters), third. The title compounds were isolated. The retention time of the peak maxima for each compound was as follows: 25 min. for compound 1F (yield 1.84 g, 9%); 60 min. for compound 1D (yield 6.62 g, 39%); 105 min. for compound 1E (yield 8.32 g, 49%).

e. 6-N-Benzoyl-2',3'-bis-O-(tert-butyldimethylsilyl) adenosine (1G):

1.74 g (2 mmole) of compound 1D was stirred with 20 ml 80% acetic acid at 22° C. After 20 h the cleavage of the monomethoxytrityl group was complete. The reaction mixture was extracted with CHCl$_3$ (3×200 ml) and washed with 200 ml 1M phosphate buffer (pH 7). The organic phase was dried over Na$_2$SO$_4$ and evaporated to dryness. Purification was accomplished using a silica gel column (2×10 cm) and eluted with CH$_2$Cl$_2$/MeOH (96/4). The light yellow product was dissolved in 5 ml CHCl$_3$ and treated with Et$_2$O until turbid. 0.982 g of the pure product crystallized out. The pure product crystallized out again from the mother liquor, 0.11 g, m.p. 189° C. The total yield was 1.092 g (91%).

EXAMPLE 1A

Chloro-octahydroazonino-p-nitrophenylethoxyphosphate a. P-nitrophenylphosphoric acid dichloride.

To phosphorus trichloride (Fluka, N.Y., #79690) (28 ml, 0.317 moles) 80 ml anhydrous ether are added. The mixture is cooled to −30° C. P-nitrophenylethanol (8.35 g, 50 mmoles) is added, followed by stirring for 1.5 hr. Ether and excess $PCl_3$ is removed under vacuum to yield p-nitrophenylphosphoric acid dichloride (yield 80%).

b. Octahydroazonin.

Caprylolactam (Fluka, N.Y., #21631) (25 g, 117 mmoles) is combined with lithium aluminum hydride (10.5 g) in ether and reduced with stirring for 5 hr. The reaction mixture is filtered and evaporated with ether. The product is octahydroazonin (90% yield).

c. 1-Trimethylsilyl octahydroazonin.

The silylamine of octahydroazonin is prepared by combining octahydroazonin (12.7 g, 0.1 moles) and trimethylsilane (0.12 moles) and 0.5 moles hexamethyldisilazane +150 mg of ammonium sulfate. The mixture is refluxed for 90 hr and distilled under vacuum to yield 16.5 g of 1-trimethylsilyl octahydroazonin (82%).

d. Chloro-octahydroazonino-p-nitrophenylethoxyphosphate.

P-nitrophenylphosphoric acid dichloride (26.8 g, 100 mmoles) and 1-trimethylsilyl octahydroazonin (19.9 g, 100 mmoles) are combined under nitrogen at 0° C. The mixture is warmed to room temperature and stirred 2–3 h. Trimethylsilyl dichloride is removed under vacuum. The product in the residue is chloro-octahydroazonino-p-nitrophenylethoxyphosphate (33.9 g, 94% yield).

EXAMPLE 2

6-N-Benzoyl-3'-O-tert-butyldimethylsilyl-5'-O-(4-ethoxytrityl)-adenosine-2'-O-(p-nitrophenylethyl)-octahydroazonino-phosphoramidite (2)

Compound 1E (0.758 g, 1.0 mmole) and diisopropylethylamine (0.52 g, 4 mmole) were dissolved in dichloromethane (5 ml) and chlorooctahydroazonino-p-nitrophenylethoxyphosphane (0.80 g, 2.22 mmole) was added dropwise. After stirring for 2 h at r.t., TLC analysis indicated complete reaction. The reaction mixture was transferred to a separatory funnel using saturated aqueous $NaHCO_3$ (50 ml) and the product was isolated by extraction with ethylacetate (2×50 ml). The organic layer was washed with saturated NaCl, dried ($Na_2SO_4$), and evaporated to dryness. The residue was dissolved in ethylacetate-triethylamine (95:5 v/v), chromatographed on a silica gel column (10×2 cm) previously calibrated with ethylacetate-triethylamine (9/1) and eluted with ethyl-acetate-triethylamine (95:5 v/v). The product fractions were collected, evaporated to dryness, finally coevaporated with dichloromethane and dried in vacuo at 40° C. to give compound 2 (1.05 g, 97%) [Anal. calcd. for $C_{59}H_{70}N_7O_9PSi.1H_2O$: C, 64.52; H, 6.60; N, 8.92. Found: C, 63.93; H, 6.85; N, 8.62].

EXAMPLE 3

6-N-Benzoyl-3'-O-tert-butyldimethylsilyl-5'-O-monoethoxytrityl-P-thioadenylyl-2'-[$O^P$-(p-nitrophenylethyl)- 5']-6-N-benzoyl-2',3'-di-O-tert-butyldimethylsilyladenosine (4A+4B)

The phosphoramidite 2 (1.12 g, 1.0 mmole) and 6-N-benzoyl-2',3'-di-tert-butyldimethylsilyladenosine (3) (0.478 g, 0.7 mmole) were dried overnight in a drying pistol at 40° C. in vacuo. The dried residue was then dissolved in dry acetonitrile (6 ml), and 3-nitro-1,2,4-triazole (0.285 g, 2.5 mmoles) was added and stirred at r.t. for 3 h. Pyridine (6 ml) and sulfur (0.5 g) were added and after stirring at r.t. for 20 h, the reaction mixture was extracted with chloroform (300 ml). The organic phase was washed with saturated NaCl-solution (2×200 ml), dried ($Na_2SO_4$), and evaporated to dryness. Final evaporation was performed with toluene to remove pyridine. The residue was dissolved in chloroform and chromatographed on a silica gel column (15×2.5 cm) with 1 liter of chloroform to give a product fraction containing both Rp and Sp isomers. The separation of the diastereoisomers was carried out on preparative silica gel plates, using dichloromethane/ethylacetate/n-hexane (1:1:1 v/v). The plates were developed thrice. The higher Rf isomer (0.47 g; 42%, TLC in dichloromethane/ethylacetate/n-hexane, 1:1:1, 0.54) and the lower Rf isomer (0.31 g; 28%, TLC in dichloromethane/ethylacetate/n-hexane, 0.46) were obtained as colorless amorphous powders after drying at 40° C. in vacuo. The higher Rf isomer was compound 4A. [Anal. calcd. for $C_{80}H_{98}N_{10}O_{14}PSi_3.1H_2O$: C, 59.89; H, 6.32; N, 9.61. Found: C, 59.89; H, 6.32; N, 9.21]. $^{31}P$-NMR (400 MHz, $CDCl_3$, 85% $H_3PO_4$, 69.841 ppm). The lower Rf isomer was compound 4B. [Anal. calcd. for $C_{80}H_{98}N_{10}O_{14}PSi_3S.1H_2O$: C, 59.89; H, 6.28; N, 9.61. Found: C, 59.91; H, 4.61; N, 9.28]. $^{31}P$-NMR (400 MHz, $CDCl_3$, 85% $H_3PO_4$, 69.223 ppm).

EXAMPLE 4

6-N-Benzoyl-3'-O-tert-butyldimethylsilyl-P-thioadenylyl-2'-[$O^P$-(p-nitrophenylethyl)-5']-6-N-benzoyl-2',3'-di-O-tert-butyldimethylsilyladenosine (5A+5B)

0.258 g, (0.164 mmole) of the pure isomers 4A and 4B, were detritylated separately by treatment of each with 2% p-toluenesulfonic acid in dichloromethane/methanol (4/1) (3.2 ml) at r.t. for 40 min. The reaction mixture was diluted with chloroform (50 ml), washed with phosphate buffer, pH 7 (2×20 ml), and evaporated to a foam. The residue was purified by silica gel column chromatography (10×2.5 cm). Compounds 5A and 5B were separated on the column by using chloroform and chloroform/methanol (100:0.5 till 100:1). The product fractions were collected and, after evaporation, dried in vacuo at 40° C. to give in the case of 5A, 0.198 g (92%), and in the case of 5B, 0.192 g (89%). 5A has an Rf of 0.27 in dichloromethane/ethylacetate/n-haxane (1:1:1). [Anal. calcd. for $C_{60}H_{82}N_{11}O_{13}PSi_3S.1H_2O$: C, 54.15; H, 6.36; N, 11.57. Found: C, 53.78; H, 6.44; N, 11.72]. 5B has an Rf of 0.30 in the same system. [Anal. calcd. for $C_{60}H_{82}N_{11}O_{13}PSi_3S$: C, 54.90; H, 6.29; N, 11.73. Found: C, 54.90; H, 6.20; N, 11.45].

EXAMPLE 5

P-Thioadenylyl-(2'-5')-adenosine (6A+6B)

The fully protected dimers 5A and 5B, respectively, were deprotected separately by the following procedure. Each protected dimer (39 mg, 0.03 mmole) was treated with 0.5M 1,8-diazabicyclo[5.4.0]undec-7-ene(1,5,5)(Fluka, cat. no. 33842, "DBU") in pyridine (9 ml), and after stirring at r.t. for 2 h was neutralized with 1M acetic acid (4.5 ml) and finally evaporated. The residue was taken up in 1M tetrabutylammonium fluoride ("$Bu_4NF$") in tetrahydrofuran ("THF") and after 24 h again evaporated to dryness. Deacetylation was achieved by treatment with conc. ammonia (20 ml) for 48 h followed by evaporation of the mixture. The residue was then dissolved in water (50 ml) and washed with chloroform (2×20 ml). The water phase was applied to a DEAE Sephadex A-25 column (60×1 cm) for elution with a linear gradient of a buffer of 0.001–0.25M $Et_3NH^+HCO_3^-$, pH 7.5. The product was eluted at a concentration of 0.08–0.1M.

Evaporation to dryness followed by coevaporation with water (10×10 ml) and final purification by paper chromatography with i-PrOH/conc. ammonia/water (7:1:2 v/v) yielded in the case of 6A 630 O.D. units (87.5%) and in the case of 6B 648 O.D. units (90%). The Rf of 6A on cellulose sheets, using the above system, was 0.29. The Rf of 6B was 0.30.

EXAMPLE 6

6-N-Benzoyl-3'-O-tert-butyldimethylsilyl-5'-O-monomethoxytrityl-P-thioadenylyl-2'-[$O^P$-(p-nitrophenylethyl)-5']-N-6-benzoyl-3'-O-tert-butyldimethylsilyl-P-thioadenylyl-2'-[$O^P$-(p-nitrophenylethyl)-5']-6-N-benzoyl-2',3'-bis-O-tert-butyldimethylsilyladenosine (7A, 7B and 8A, 8B)

The phosphitamide 2 (0.449 g; 0.41 mmole) was condensed with the 5'-hydroxy dimer 5A and 5B (0.0262 g; 0.2 mmole) separately in the presence of 3-nitro-1,2,4-triazole (0.114 g; 1.0 mmole) in dry acetonitrile (3.2 ml). After stirring at r.t. for 3 h, sulfur (0.2 g; 6.25 mmole) in pyridine (0.4 ml) was added for oxidation. After stirring at r.t. for another 24 h, the product was extracted with dichloromethane (50 ml), the organic phase was washed with saturated NaCl solution (2×20 ml), dried ($Na_2SO_4$), and then evaporated to dryness. Final coevaporation was performed with toluene to remove pyridine. The crude product was chromatographed on a silica gel column (15×2 cm) and eluted with chloroform/methanol (100:2) to give, on condensing with compound 5A, the isomer mixture 7A+7B. The isomer mixture 8A+8B, was obtained upon condensing the phosphitamide 2 with compound 5B in the same manner. The diastereomeric separation of each isomer mixture was accomplished by using preparative silica gel plates (20×20×0.2 cm) to which about 50 mg of isomer mixture per plate was applied for optimal separation. The plates were developed in dichloromethane/ethylacetate/n-hexane (1:1:0.5 v/v) three times. The appropriate bands were cut out and eluted with chloroform/methanol (4:1). The higher Rf isomer synthesized from 5A has a Rf of 0.58 in dichloromethane/ethylacetate/n-hexane (1:1:1) and yielded 48% (0.218 g) of 7A. [Anal. calcd. for $C_{111}H_{135}N_{17}O_{22}P_2Si_4S_2 \cdot 1H_2O$: C, 57.56; H, 5.96; N, 10.28. Found: C, 57.38; H, 5.99; N, 10.11]. The lower Rf isomer has a Rf of 0.48 in the above-mentioned system, and yielded 34% (0.157 g) of 7B. [Anal. calcd. for $C_{111}H_{135}N_{17}O_{22}P_2Si_4S_2 \cdot 1H_2O$: C, 57.56; H, 5.96; N, 10.28. Found: C, 57.40; H, 5.97; N, 10.19].

The isomeric mixture derived from the 5'-hydroxy dimer 5B was separated in the same manner and yielded the higher Rf isomer 8A in 41% (0.186 g) with an Rf of 0.53 in the above solvent system. [Anal. calcd. for $C_{111}H_{135}N_{17}O_{22}P_2Si_4S_2$: C, 58.02; H, 5.92; N, 10.36. Found: C, 58.00; H, 5.84; N, 10.66]. The lower Rf isomer 8B showed a Rf value of 0.45 and yielded 35% (0.161 g). [Anal. calcd. for $C_{111}H_{135}N_{17}O_{22}P_2Si_4S_2 \cdot 1H_2O$: C, 57.56; H, 5.96; N, 10.28. Found: C, 57.30; H, 5.78; N, 10.03].

EXAMPLE 7

(Rp)-P-Thioadenylyl-(2'-5')-(Rp)-P-thioadenylyl-(2'-5')-adenosine (9A)

A solution of 0.116 g (0.05 mmole of the fully protected trimer 7A was detritylated with 2% p-toluenesulfonic acid in 1.5 ml dichloromethane/methanol (4:1) for 90 min. The mixture was dissolved in $CHCl_3$, washed with phosphate buffer (2×15 ml), dried ($Na_2SO_4$), and evaporated to dryness. The residue was chromatographed on silica gel plates (20×20×0.2 cm), developed with dichloromethane/ethylacetate/n-hexane (5:5:3 v/v). The product band ($R_f$ 0.35) was cut out, eluted with chloroform/methanol (7:5) and gave on evaporation to a colorless foam a yield of 70–83%. 38.5 mg (18.9 micromole) of the product was then stirred with 0.5M DBU in pyridine (7.5 ml) for 20 h, neutralized with 1M acetic acid (3.75 ml) and finally evaporated. The evaporated product was desilylated through treatment with 1M $Bu_4NF$ in THF (6 ml) for 24 h. The mixture was concentrated in vacuo. The residue was dissolved in conc. ammonia (25 ml) and stirred at r.t. for 48 h. After evaporating the solution, the residue was taken up in water (20 ml) and washed with chloroform (2×10 ml). The aqueous phase was put on a DEAE Sephadex A-25 column (60×1 cm) and the product was eluted with a linear gradient of $Et_3NH^+HCO_3^-$-buffer. The product fraction was collected, evaporated and further purified by paper chromatography using i-PrOH/conc. ammonia/water (6:1:3) to give the title compound in 75–80% yield.

EXAMPLE 8

(Sp)-P-Thioadenylyl-(2'-5')-(Rp)-P-thioadenylyl-(2'-5')-adenosine (9B)

A solution of 0.116 g (0.05 mmole) of the fully protected trimer 7B was subjected to the procedure of Example 7. The title compound was obtained in 75–80% yield.

EXAMPLE 9

(Rp)-P-Thioadenylyl-(2'-5')-(Sp)-P-thiodenylyl-(2'-5')-adenosine (10A)

A solution of 0.116 g (0.05 mmole) of the fully protected trimer 8A was subjected to the procedure of Example 7. The title compound was obtained in 75–80% yield.

EXAMPLE 10

(Sp)-P-Thioadenylyl-(2'-5')-(Sp)-P-thioadenylyl-(2'-5')-adenosine (10B)

A solution of 0.116 g (0.05 mmole) of the fully protected trimer 8B was subjected to the procedure of Example 7. The title compound was obtained in 75–80% yield.

The UV-absorption spectra in methyl alcohol and $^1$H-NMR spectra of the above-prepared protected monomer, dimer and trimer cores are set forth in Tables 1 and 2, respectively.

TABLE 1

UV-Absorption Spectra of Protected Monomer, Dimer and Trimer Cores in MeOH

| Compound | $\lambda_{max}$ | (nm) |      | l gε |
|----------|-----------------|------|------|------|
| 2        | 230             | 277  | 4.47 | 4.50 |
| 4A       | 231             | 277  | 4.66 | 4.70 |
| 4B       | 231             | 277  | 4.66 | 4.70 |
| 5A       |                 | 278  |      | 4.70 |
| 5B       |                 | 278  |      | 4.70 |
| 7A       | 230             | 278  | 4.78 | 4.90 |
| 7B       | 230             | 278  | 4.78 | 4.89 |
| 8A       | 230             | 278  | 4.79 | 4.90 |
| 8B       | 230             | 278  | 4.78 | 4.90 |

TABLE 2

$^1$H-NMR Spectra of Protected Monomer, Dimer and Trimer Cores[1]

| Compound | 1'-H | | | 2-H | 8-H | Solvent |
|---|---|---|---|---|---|---|
| 2 | 6.11 | 6.13 | | 8.70 | 8.23 | CDCl$_3$ |
| 4A | 6.30d | 5.87d | | 8.68; 8.60 | 8.19; 8.17 | CDCl$_3$ |
| 4B | 6.29d | 5.94d | | 8.72; 8.62 | 8.26; 8.18 | CDCl$_3$ |
| 5A | 6.06d | 5.94d | | 8.82; 8.75 | 8.25; 8.08 | CDCl$_3$ |
| 5B | 6.13d | 5.90d | | 8.74; 8.73 | 8.26; 8.24 | CDCl$_3$ |
| 7A | 6.23d | 6.08d | 5.84d | 8.69; 8.58; 8.55; | 8.20; 8.11; 8.01 | CDCl$_3$ |
| 7B | 6.22d | 6.17d | 5.85d | 8.67; 8.60; 8.57; | 8.23; 8.10; 8.00 | CDCl$_3$ |
| 8A | 6.27d | 6.13d | 5.93d | 8.71; 8.61; 8.60; | 8.21; 8.13; 8.00 | CDCl$_3$ |
| 8B | 6.27d | 6.22d | 5.90d | 8.71; 8.64; 8.61; | 8.27; 8.22; 8.19 | CDCl$_3$ |

[1]δ values in ppm; Standard TMS; characteristic signals

Assignment of Absolute Configuration of 2',5'-Phosphorothioate Adenylate Trimer Cores Determination of the absolute configurations of the trimer cores was accomplished by $^{31}$P-NMR fast bombardment mass spectrometry and enzymatic digestion.

It is known that the enzyme SVPD preferentially cleaves Rp-3',5'- or 2',5'-phosphorothioate linkages from the 2'/3'-terminus. Nelson et al, *J. Org. Chem.* 49:2314–2317 (1984); Eppstein et al, *J. Biol. Chem.* 261:5999–6003 (1986); Lee et al, *Biochemistry* 24:551–555 (1985). SVPD hydrolysis of the chemically synthesized dimer core A$_{Rp}$A yielded adenosine and AMPS in a molar ratio of 1:1, respectively; the half-life was 3 hours (Table 3). The A$_{Sp}$A dimer core was not a substrate for SVPD under these conditions. Trimer core 9A has the RpRp internucleotide linkage configuration as determined by hydrolysis by SVPD to yield AMPS plus A$_{Rp}$A in a molar ratio of 1:1, respectively. Similarly, SVPD hydrolysis of trimer core 9B yielded A$_{Sp}$A and AMPS, thus identifying trimer core 9B as having the SpRp internucleotide linkage configuration (Table 3). Trimer cores 10A and 10B were not substrates for SVPD (Table 3), revealing the presence of the Sp configuration in the internucleotide linkage adjacent to the 2'/3'-termini.

The four 2,5-phosphorothioate adenylate trimer cores were further characterized by hydrolysis with the enzyme 2'-phosphodiesterase ("2'-PDE"), an exoribonuclease found in L cell extract The enzyme cleaves from the 2'/3'-terminus. Whereas authentic A$_2$ and A$_3$ cores where hydrolyzed to adenosine and AMP with a half-life of 10 min, the dimer cores A$_{Rp}$A and A$_{Sp}$A were not substrates for 2'-PDE (Table 3). The fact that the 2,5-phosphorothioate dimer cores were not substrates for 2'-PDE (unlike authentic 2-5A) greatly assisted in the assignment of the stereoconfigurations of the 2',5'-phosphorothioate adenylate trimer cores. Trimer core 9A was a substrate for 2'-PDE; the products of hydrolysis were A$_{Rp}$A and AMPS. Trimer core 9B was a substrate for SVPD, yielding A$_{Sp}$A and AMPS; trimer core 10A was a substrate, yielding A$_{Rp}$A and AMPS; trimer 10B was not a substrate for 2'-PDE.

$^{31}$P-NMR spectroscopy has revealed that Sp stereoisomers of phosphorothioates resonate to higher field than Rp diastereomers. Further, Sp diastereomers have a longer retention time on reverse phase HPLC than Rp diastereomers. The A$_{Sp}$A dimer core resonates upfield from the A$_{Rp}$A (Table 3). Similarly, two singlets observed for A$_{Sp}$A$_{Sp}$A resonate upfield from the two singlets observed for A$_{Rp}$A$_{Rp}$A (Table 3). Assignment of the absolute configura-

TABLE 3

Analytical Data, Dimer and Trimer 2,5-Phosphorothioate Adenylate Cores

| | | | Hydrolysis by: | | | | | | |
|---|---|---|---|---|---|---|---|---|---|
| | | | SVPD | | L cell extract | | serum phosphodiestrereases | | Stereoconfiguration assigned |
| 2,5-Phosphorothioate | $^{31}$P-NMR (PPM[a]) | R$_T$ (min[d]) | dimer core isolated | half life | dimer core isolated | half life | dimer core isolated | half life | |
| Dimer Cores | | | | | | | | | |
| 6A | 57.63 | 19.5 | — | 3 h | not cleaved | | not cleaved | | Rp |
| 6B | 56.13 | 24.2 | not cleaved | | not cleaved | | not cleaved | | Sp |
| Trimer Cores | | | | | | | | | |
| 9A | 57.45, 57.71 | 30.5 | Rp | 1 h | Rp | 18 h | Rp | 8 h | RpRp[b] |
| 9B | 57.55, 56.62 | 33.0 | Sp | 8 H | Sp | 15 H | not cleaved | | SpRp[c] |
| 10A | 56.34, 57.54 | 35.2 | not cleaved | | Rp | 20 days | not cleaved | | RpSp[c] |
| 10B | 56.50, 56.26 | 39.5 | not cleaved | | not cleaved | | not cleaved | | SpSp[b] |
| A$_3$ core | 14.5 | — | 5 min | — | 10 min | — | 10 min | | |
| A$_2$ core | | | ND | | — | 10 min | ND | | |

[a]decoupled spectra
[b]assignment confirmed by coupled and decoupled $^{31}$P-NMR
[c]assignment confirmed by coupled $^{31}$P-NMR and enzymatic hydrolyses
[d]HPLC retention times tions of trimer cores 9A ($\underline{Rp}\underline{Rp}$) and 10B ($\underline{Sp}\underline{Sp}$) was based on the two singlets which resonate at the same frequency as the singlets observed for the $A_{Rp}A$ and $A_{Sp}A$ dimer cores. Assignment of configurations for trimer cores 9B and 10A was made in combination with the enzyme degradations and HPLC analyses (Table 3). The $^{31}$P-NMR spectra revealed that the $\delta$ ppm between the two singlets for the $A_{Sp}A_{Rp}A$ trimer core is 1.2, whereas the two singlets for the $A_{Rp}A_{Sp}A$ have $\delta$ ppm of 0.8 (assignment is 5' to 2'/3' terminus)

The metabolic stability of the 2,5'-phosphorothioate dimer and trimer cores is markedly greater than authentic 2-5A. The rate of hydrolysis of the trimer cores by the 3'-exonuclease SVPD is, in order of decreasing stability: $A_{Sp}A_{Rp}A > A_{Rp}A_{Rp}A >>> A_3$. The trimer cores $A_{Rp}A_{Sp}A$ and $A_{Sp}A_{Sp}A$ are not substrates of SVPD (Table 3). The 3'->5' direction of stepwise cleavage by SVPD is blocked by an $\underline{Sp}$ configuration, preventing cleavage of the upstream adjacent phosphorothioate linkage. With 2'-PDE, the $A_{Rp}A_{Rp}A$, $A_{Sp}A_{Rp}A$ and $A_{Rp}A_{Sp}A$ trimer cores, but not the $A_{Sp}A_{Sp}A$ trimer core, were substrates. With both SVPD and 2'-PDE, the dimer cores (either $A_{Rp}A$ or $A_{Sp}A$) accumulate following hydrolysis of the $A_{Rp}A_{Rp}A$, $A_{Sp}A_{Rp}A$ and $A_{Rp}A_{Sp}A$ trimer cores. Hydrolysis of the 2-5A molecule by SVPD and 2'-PDE proceeds from the 2'/3'-terminus. Therefore, introduction of the phosphorothioate group into the trimer core results in the accumulation of the $A_{Rp}A$ or $A_{Sp}A$ dimer cores from the 5'-terminus and the accumulation of AMPS from the 2'/3'-terminus (Table 3). With authentic $A_3$, there is no detectable accumulation of $A_2$ following hydrolysis by SVPD or 2'-PDE.

None of the $\underline{Sp}$ linkage-containing trimer cores were cleaved by SVPD. While the half-life of $A_{Sp}A_{Rp}A$ upon cleavage by L-cell extract (15 hours) did not differ significantly from that of $A_{Rp}A_{Rp}A$ (18 hours), the half-life for the $A_{Rp}A_{Sp}A$ trimer was orders of magnitude longer (20 days). $A_{Sp}A_{Sp}A$ was not cleaved by L-cell extract (Table 3).

Preparation of Phosphorothioate Tetramer Cores

The following non-limiting examples illustrate the preparation of the fully-resolved tetramer core compounds of the invention.

EXAMPLE 11 a. (Sp)-P-Thioadenylyl-(2'-5')-(Sp)-P-thioadenylyl-(2'-5')-(Sp)-P-thiodenylyl-(2'-5)-adenosine b. (Rp)-P-thiodenylyl-(2'-5')-(Sp)-P-thioadenylyl-(2'-5')-(Sp)-P-thiodenylyl-(2'-5')-adenosine A solution of 0.149 g (0.065 mmole) of fully protected trimer 8B, which has the stereoconfiguration $\underline{Sp}\underline{Sp}$, was detritylated with 2% p-toluenesulfonic acid in 1.5 ml dichloromethane/methanol (4:1) for 3 h at room temperature. The mixture was diluted with 50 ml CHCl$_3$, washed with phosphate buffer (2×15 ml), dried (Na$_2$SO$_4$), and evaporated to dryness. The residue was chromatographed on silica gel plates (20×20×0.2 cm) developed with dichloromethane/ethylacetate/n-hexane (5:5:3 v/v). The product band, R$_f$ 0.55, was cut out, eluted with chloroform/ethanol (1:1) and gave, on evaporation to a colorless foam of 0.108 g (yield 88%). The 5'-deblocked $\underline{Sp}\underline{Sp}$ trimer 8B (101 mg; 0.05 mM) was dissolved in 0.5 ml acetonitrile overnight with phosphitamide 2 (0.105 g; 0.1 mmole). 3-Nitro-1,2,4-triazole (0.023 g; 0.2 mmole) was added. After stirring at room temperature for 3 h, sulfur (0.042 g; 1.3 mmole) in pyridine (0.084 ml) was added for oxidation. After stirring at room temperature for another 24 h, the product was extracted with dichloromethane (50 ml), the organic phase was washed with saturated NaCl solution (2×20 ml), dried over Na$_2$SO$_4$, and then evaporated to dryness. Final coevaporation was performed with toluene to remove pyridine. The crude product was purified by using preparative silica gel plates (20×20×0.2 cm) to which about 50 mg per plate was applied for optimal separation by developing in dichloromethane/ethylacetate/n-hexane (1:1:0.5 v/v) three times. The band containing the fully protected $\underline{Sp}\underline{Sp}\underline{Sp}$ tetramer (R$_f$ 0.3) and the band containing the fully protected $\underline{Rp}\underline{Sp}\underline{Sp}$ tetramer (R$_f$ 0.4), were cut out and eluted with chloroform/methanol (4:1). The yield of the fully protected $\underline{Sp}\underline{Sp}\underline{Sp}$ tetramer was 43 mg; 29%. The yield of the fully protected $\underline{Rp}\underline{Sp}\underline{Sp}$ compound was 53 mg; 35.5%. The two isomers (7.3 micromoles; 0.22 mg) were deblocked by stirring with 0.5M DBU in pyridine (5.0 ml) for 20 h, neutralized with 1M acetic acid/pyridine (0.5 ml) and finally evaporated. The subsequent desilylation was achieved with 1M tetrabutylammonium fluoride in tetrahydrofuran (3.6 ml) for 48 h at r.t. The mixture was concentrated in vacuo, the residue dissolved in conc. ammonia (15 ml) and stirred at r.t. for 48 h. After evaporating the solution, the residue was taken up in 5 ml of 80% acetic acid and allowed to stand for 20 h at r.t. The residue was dissolved in about 5 ml water and put on a DEAE Sephadex A-25 column (60×1 cm) and the product was eluted with a linear gradient of Et$_3$NH$^+$HCO$_3^-$ buffer (pH 7.5) (gradient 0.001–1M). The product fractions were collected, evaporated and further purified by paper chromatography using; i-PrOH/conc. ammonia/water (6:1:3). The tetramer isomers were eluted with water to give $A_{Sp}A_{Sp}A_{Sp}A$ (72% yield; R$_f$ 0.23) and $A_{Rp}A_{Sp}A_{Sp}A$ (73% yield; R$_f$ 0.29) as the ammonium salt.

EXAMPLE 12 a. (Rp)-P-Thioadenylyl-(2'-5')-(Rp)-P-thioadenylyl-(2'-5')-(Rp)-P-thioadenylyl-(2'-5')-adenosine b. (Sp)-P-Thioadenylyl-(2'-5')-(Rp)-P-thioadenylyl-(2'-5')-(Rp)-P-thioadenylyl-(2'-5')-adenosine The title compounds are prepared by following the procedure of Example 11, but substituting the fully protected trimer 7A for 8B as the starting material.

EXAMPLE 13 a. (Rp)-P-Thioadenylyl-(2'-5')-(Sp)-P-thioadenylyl-(2'-5')-(Rp)-P-thioadenylyl-(2'-5')-adenosine b. (Sp)-P-Thioadenylyl-(2'-5')-(Sp)-P-thioadenylyl-(2'-5')-(Rp)-P-thioadenylyl-(2'-5')-adenosine The title compounds are prepared by following the procedure of Example 11, but substituting the fully protected trimer 7B for 8B as the starting material.

EXAMPLE 14 a. (Sp)-P-Thioadenylyl-(2'-5')-(Sp)-P-thioadenylyl-(2'-5')-(Sp)-P-thioadenylyl-(2'-5')-adenosine b. (Sp)-P-Thioadenylyl-(2'-5')-(Sp)-P-thioadenylyl-(2'-5')-(Sp)-P-thioadenylyl-(2'-5')-adenosine The title compounds are prepared by following the procedure of Example 11, but substituting the fully protected trimer 8A for 8B as the starting material.

Preparation of 2',5'-Phosphorothioate Oligoadenylate 5'-Monophosphates

5'-Monophosphates of 2',5'-oligoadenylates are readily prepared by reacting the corresponding core compounds with $POCl_3$. Such treatment would result in the elimination of sulfur from the phosphorothioate internucleotide linkages of the compounds of the present invention, and the formation of 2-5A. Thus, the 5'-monophosphates of the phosphorothioate oligoadentylates must be prepared from the corresponding fully protected core compounds from which the monomethoxytrityl blocking group on the 5'-terminal nucleotide has been removed. The conditions of the phosphorylation must be such that the p-nitrophenylethyl blocking groups on the internucleotide phosphorous atoms remain intact.

The 5'-monophosphate of each resolved trimer core of the present invention was prepared from the 5'-hydroxy analogue of the corresponding fully protected trimer 7A, 7B, 8A or 8B. The intermediate 5'-phosphotriester (11A, 11B, 12A or 12B) was prepared according to Example 15 and then freed of all blocking groups according to Example 16 to yield the 5'-monophosphate. The procedure of Examples 15 and 16 may be used for forming the 5'-monophosphate of any of the four trimer core stereoisomers.

EXAMPLE 15

5'-O-(2,5-Dichlorophenyl-p-nitrophenylethyl)-phosphoryl-6-N-benzoyl-3'-O-tert-butyldimethylsilyl-P-thioadenylyl-2'-[$O^P$-(p-nitrophenylethyl)-5']-6-N-benzoyl-3'-O-tert-butyldimethylsilyl-P-thioadenylyl-2'-[$O^P$-(p-nitrophenylethyl)-5']-6-N-benzoyl-2',3'-di-O-tert-butyldimethylsilyl adenosine (11A, 11B, 12A or 12B)

To a solution of 1,2,4-triazole (0.011 g; 0.16 mmole) and 2,5-dichlorophenylphosphorodichloridate (0.022 g; 0.078 mmole) in dry pyridine (0.5 ml) was added the 5'-deblocked analogue of either 7A, 7B, 8A or 8B (0.1 g; 0.049 mmole) (prepared as an intermediate in Example 11), and after stirring for 30 min, p-nitrophenylethanol (0.02 g; 0.119 mmole) was added and stirring continued for 20 h. The situation was then extracted with chloroform (50 ml), the organic phase was washed with water (2×20 ml), evaporated to dryness, and finally co-evaporated with toluene. The residue was purified by silica gel chromatography on preparative plates (20×20×0.2 cm) using the system dichloromethane/n-hexane/ethylacetate (1:1:1 v/v). The product band was eluted with chloroform/methanol (4:1) and evaporated in vacuo to give 11A, 11B, 12A or 12B in 70–80% yield, respectively.

EXAMPLE 16 a. 5'-O-Phosphoryl-(Rp)-thioadenylyl-(2'-5')-(Rp)-thioadenylyl-(2'-5')-adenosine (13A)

b. 5'-O-Phosphoryl-(Sp)-thioadenylyl-(2'-5')-(Rp)-thioadenylyl-(2'-5')-adenosine (13B)

c. 5'-O-Phosphoryl-(Rp)-thioadenylyl-(2'-5')-(Sp)-thioadenylyl-(2'-5')-adenosine (14A)

d. 5'-O-Phosphoryl-(Sp)-thioadenylyl-(2'-5')-(Sp)-thioadenylyl-(2'-5')-adenosine (14B)

p-Nitrobenzaldoxime (0.036 g; 0.216 mmole) was stirred for 30 min in dioxane/triethylamine/water (each 0.5 ml), the appropriate 5'-phosphotriester 11A, 11B, 12A or 12B (0.05 g, 0.02 mmole) was added and the mixture was kept at r.t. for 4 h. The solution was evaporated to dryness, followed by coevaporation with toluene (2×5 ml), and the residue purified by preparative TLC on plates (20×20×0.2 cm) in chloroform/methanol (95:5). The product band was eluted with chloroform/methanol/triethylamine (5:1:1) and evaporated to dryness. This material (0.022 g; 10 micromole) was stirred with 0.5M DBU in pyridine (8 ml) at r.t. for 24 h, the solution neutralized with 1M acetic acid (4 ml) and evaporated to dryness. The residue was treated with 1M $Bu_4NF$ in THF (6 ml) for 48 h and after evaporation the debenzoylation was accomplished by treatment with conc. ammonia (25 ml) at r.t. for 48 h. The solution was evaporated. The deblocked crude trimer 5'-monophosphate was taken up in water (25 ml) and washed with chloroform (2×10 ml). The aqueous phase put on a DEAE Sephadex A-25 column (60×1 cm) for elution with a linear gradient of 0.001–1M $Et_3NH^+HCO_3^-$ buffer. The product fractions were collected, evaporated to dryness, and after several coevaporations with water were further purified by paper chromatography using the i-PrOH/conc ammonia/water-system (55:10:35). The product band was eluted with water and gave on lyophilization the trimeric P-thioadenylate 5'-monophosphate 13A, 13B, 14A or 14B as ammonium salts in 68–74% yield.

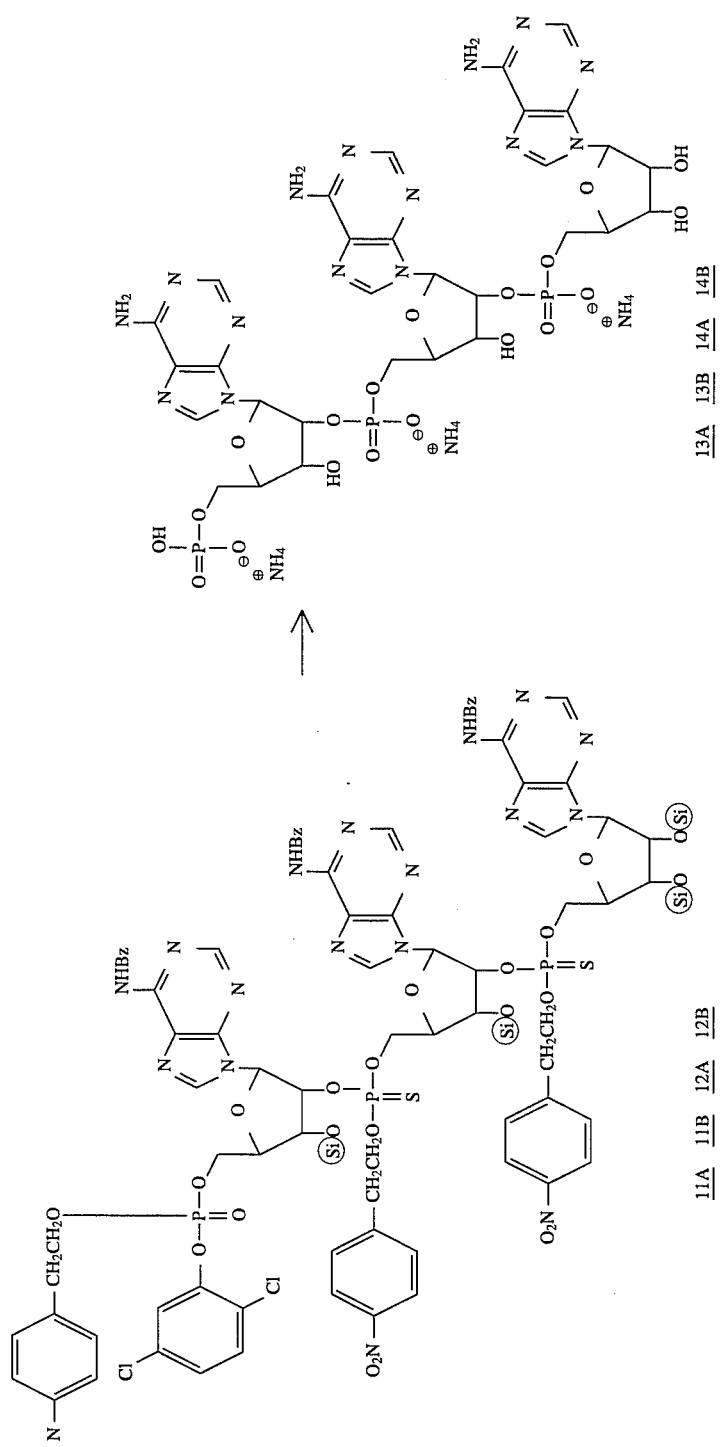

The $^1$H-NMR of the 5'-monophosphates are as follows:

TABLE 4

$^1$H-NMR Spectra of 5'O-Phosphoryl-
P-thioadenylyl-(2'-5')-P-thioadenylyl
-(2'-5')-adenosine Stereoisomers[2]

| Compound | 1'-H | 2-H | 8-H | Solvent |
|---|---|---|---|---|
| 13A | 6.04 5.92d 5.75d | 8.31; 8.18; 8.12; | 7.98; 7.85; 7.80 | D$_2$O |
| 13B | 6.12s 5.94d 5.76d | 8.26; 8.21; 8.11; | 7.99; 7.94; 7.86 | D$_2$O |
| 14A | 6.03s 5.92d 5.80d | 8.27; 8.22; 8.15; | 8.04; 7.93; 7.81 | D$_2$O |
| 14B | 6.09s 5.94s 5.81d | 8.41; 8.26; 8.14; | 8.07; 8.02; 7.89 | D$_2$O |

[2]δ values in ppm; Standard TMS; characteristic signals

Monophosphorylation of the 5'-deblocked protected trimers to form the 5'-phosphotriesters 11A, 11B, 12A or 12B proceeds in high yield, 70–80%, followed by the further high yield (68–74%) step of complete deprotection resulting in the trimer 5'-monophosphates 13A, 13B, 14A or 14B.

The 5-monophosphates of each resolved tetramer core compound of the present invention is prepared in the same fashion, using the identical molar quantities as in Examples 15 and 16 except that the starting material for the synthesis is the 5'-hydroxy analogue of the fully protected tetramer rather than the 5'-hydroxy analogue of the fully protected trimer. The following fully resolved tetramer 5'-monophosphates are thus prepared:

5'-O-Phosphoryl-(Rp)-thioadenylyl-(2'-5')-(Rp)-thioadenylyl-(2'-5')-(Rp)-thioadenylyl-(2'-5')-adenosine 5'-O-Phosphoryl-(Rp)-thioadenylyl-(2'-5')-(Rp)-thioadenylyl-(2'-5')-(Sp)-thioadenylyl-(2'-5')-adenosine 5'-O-Phosphoryl-(Rp)-thioadenylyl-(2'-5')-(Sp)-thioadenylyl-(2'-5')-(Sp)-thioadenylyl-(2'-5')-adenosine 5'-O-Phosphoryl-(Sp)-thioadenylyl-(2'-5')-(Sp)-thioadenylyl-(2'-5')-(Sp)-thioadenylyl-(2'-5')-adenosine 5'-O-Phosphoryl-(Sp)-thioadenylyl-(2'-5')-(Sp)-thioadenylyl-(2'-5')-(Rp)-thioadenylyl-(2'-5')-adenosine 5'-O-Phosphoryl-(Sp)-thioadenylyl-(2'-5')-(Rp)-thioadenylyl-(2'-5')-(Rp)-thioadenylyl-(2'-5')-adenosine 5'-O-Phosphoryl-(Sp)-thioadenylyl-(2'-5')-(Sp)-thioadenylyl-(2'-5')-(Rp)-thioadenylyl-(2'-5')-adenosine 5'-O-Phosphoryl-(Rp)-thioadenylyl-(2'-5')-(Sp)-thioadenylyl-(2'-5')-(Rp)-thioadenylyl-(2'-5')-adenosine Preparation of 2',5'-Phosphorothioate
Oligoadenylate 5'-Diphosphates and
5'-Triphosphates The 5'-diphosphate and 5-triphosphate of the 2',5'-phosphorothioate oligoadenylates may be prepared from the 5'-monophosphate by following the procedure of Example 17.

EXAMPLE 17

All reactions are performed in glassware oven-dried at 125° C. for 18–24 hr. A 2',5'-phosphorothioate oligoadenylate stereoisomer (trimer or tetramer, 400 OD units at 260 nm) is dissolved in 500 microliters of dry dimethylformamide ("DMF") and dried in vacuo in a 10 ml conical flask at 35° C. This process is repeated three times. To the dry residue, 50 micromoles of triphenylphosphine, 100 micromoles of imidazole and 50 micromoles of dipyridinyl disulfide are added. The mixture is dissolved in 500 microliters dry DMF plus 50 microliters of dry dimethylsulfoxide. The solution is stirred with a stirring bar for 2 hr at room temperature. After 2 hr the solution is homogeneous (after 30 minutes, the solution begins to change to yellow). The solution is transferred dropwise to 10 ml of a 1% NaI/dry acetone (w/v) solution. The clear white precipitate which forms is the sodium salt of the 5'-phosphoroimidazolidate. The precipitate is centrifuged at room temperature, the supernatant is decanted, and the precipitate is washed three times with 10 ml dry acetone. The centrifuging is repeated. The precitipate is dried over P$_2$O$_5$ in vacuo for 2 hr. The precipitate is dissolved in 200 microliters of freshly prepared 0.5M tributylammonium pyrophosphate in dry DMF. The solution is maintained at room temperature for 18 hr after which time the DMF is removed in vacuo. The residue is dissolved in 0.25M triethylammonium bicarbonate buffer ("TEAB") (pH 7.5). The 5'-di and 5'-triphosphate products are separated using a DEAE-Sephadex A25 column (HCO$_3^-$ form; 1×20 cm) with a linear gradient of 0.25M to 0.75M TEAB. Fractions (10 ml) are collected. The product is observed by ultraviolet spectroscopy at 254 nm. The fractions containing the 5'-di- and 5'-triphosphates are separately pooled and dried in vacuo. The TEAB is removed by repeated addition of water followed by lyophilization. The yield of the 5'-diphosphate is about 5%; the yield of the 5'-triphosphate is about 60%.

It is generally regarded that activation of RNase L by 2-5A is key to the antiviral defense mechanisms. Interferon induces transcription of the enzyme 2-5A synthetase which produces 2',5' linked oligoadenylates upon activation of double-stranded RNA. The only known biochemical effect of 2-5A is activation of RNase L. This enzyme hydrolyses mRNA and rRNA, thereby resulting in inhibition of protein synthesis. The activation of RNase L is transient unless 2-5A is continuously synthesized, since 2-5A is rapidly degraded. RNase L activation thus plays a critical role in inhibiting replication, and therefore in defending against infection by viruses.

According to the invention, all four of the 2',5'-phosphorothioate adenylate trimer cores, and their 5'-monophosphates bind to RNase L, as determined by radio binding assay according to the method of Knight et al, Meth. Enzymol. 79:216–227 (1981). The 2',5'-phosphorothioate adenylate trimer cores and authentic A$_3$ were able to displace p$_3$A$_4$[$^{32}$P]pCp probe from RNase L in L929 cell extracts in a concentration-dependent manner (FIG. 1A). IC$_{50}$s varied from 2×10$^{-6}$ to 5×10$^{-6}$M. However, the 5'-monophosphorylated trimers had 1000-fold higher binding affinity to RNase L than their respective cores, that is, IC$_{50}$s ranged from 2×10$^{-9}$ to 5×10$^{-9}$M (FIG. 1A). Without wishing to be bound by any theory, this increase may be attributed to the ability of the 5'-monophosphates to anchor the molecule to RNase L more effectively because of increased polarity.

Figure 1B:
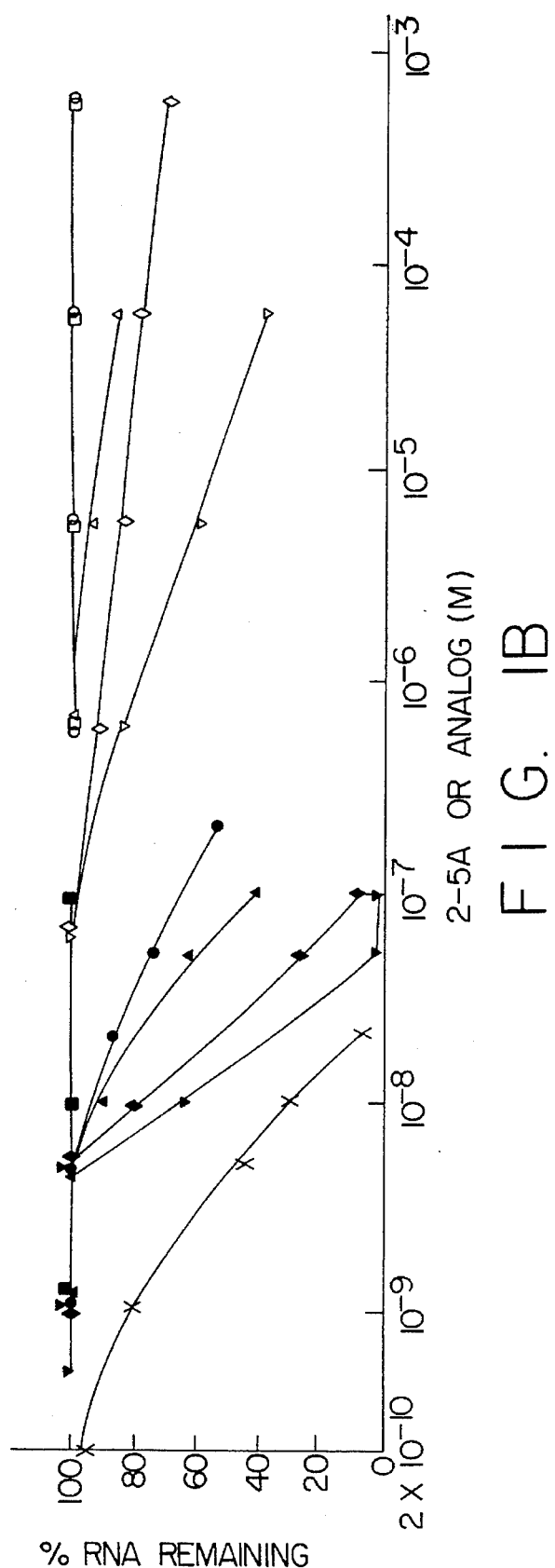
FIG. 1B represents the results of a core-cellulose assay indicating the ability of the 2',5'-phosphorothioate adenylate trimer cores and 5'-monophosphates to activate partially-purified RNase L from L929 cell extracts to hydrolyze the substrate polY(U)-3'-[$^{32}$P]pCp. Activation of RNase L was determined by conversion of poly (U )-3'-[$^{32}$P]pCp to acid-soluble fragments. 100% represents 30,000 cpm of labelled poly(U)-3'-[$^{32}$P]pCp bound to glass fiber filters. The curves are labelled in the same manner as FIG. 1A.

The 2',5'-phosphorothioate cores, with one exception, have the correct stereoconfiguration to activate RNase L. The activation of partially-purified RNase L by the 2',5'-phosphorothioates was measured according to the core-cellulose assay of Silverman, *Analyt. Biochem.* 144:450–460 (1985) which relies on hydrolysis of the substrate poly(U)-3'-[$^{32}$P]pCp. Surprisingly, three of the four 2',5'-phosphorothioate adenylate cores were able to activate RNase L to cleave poly(U)-3'-[$^{32}$P]pCp in the core-cellulose assay. (FIG. 1B) The order of activation of the trimer cores and the corresponding 5'-monophosphates is: RpRp>SpRp>RpSp (FIG. 1B). While $pA_{Rp}A_{Rp}A$ was the most efficient activator of RNase L, the compound is metabolically unstable and is readily attacked by phosphodiesterases (See Table 3). The SpSp trimer core did not activate RNase L, even at a concentration of $10^{-3}$M. As was observed in the binding assay (FIG. 1A), there was a 1000-fold increase in the activation of RNase L by the 5'-monophosphates of the 2',5'-phosphorothioate trimers compared to their respective cores.

Activation of RNase L by 2',5'-phosphorothioate adenylate trimer cores and their 5'-monophosphates was also measured in an rRNA cleavage assay using L929 cell extracts. $A_{Rp}A_{Rp}A$ and $A_{Sp}A_{Rp}A$ activated RNase L to cleave 28S and 18S rRNA to specific cleavage products at $10^{-5}$M. However, $A_{Rp}A_{Sp}A$ and $A_{Sp}A_{Sp}A$ did not activate RNase L at concentrations as high as $10^{-4}$M. It appears that the rRNA cleavage assay was not sensitive enough to detect activation of RNase L by $A_{Rp}A_{Sp}A$. Under the experimental conditions used, authentic $A_3$ core was also inactive, which is in agreement with previous reports (Haugh et al, *Eur. J. Biochem.* 132:77–84 (1983)).

The corresponding 5'-monophosphates $pA_{Rp}A_{Rp}A$, $pA_{Sp}pA_{Rp}A$ (at $10^{-8}$M) and $pA_{Rp}A_{Sp}A$ (at $10^{-7}$M) activated RNase L to cleave 28S and 18S rRNA. Authentic $pA_3$ was active at $10^{-6}$M. Incubation with $pA_{Sp}A_{Sp}A$, even at concentrations as high at $10^{-5}$M, did not result in detectable rRNA degradation.

The increased bonding strength of the 5'-phosphorylated trimer core $A_{Rp}A_{Sp}A$ provides a relatively metabolically stable and highly efficient activator for RNase L.

$A_{Sp}A_{Sp}A$ and corresponding 5'-monophosphate were observed to inhibit RNase L activation in both the core-cellulose and rRNA cleavage assays. Notwithstanding, these compounds are extremely useful as probes in the evaluation of the role of PNase L in the interferon-induced biological cascade. Most importantly, $pA_{Sp}A_{Sp}A$ selectively inhibits activation of RNase L at physiological concentrations, and is metabolically stable to specific and non-specific phosphodiesterases. The molecule provides the means to selectively shut off RNase L activation.

Individuals afflicted with chronic myelogenous leukemia ("CML") display a highly elevated RNase L activity, as evidenced by novel rRNA CML-specific cleavage products. Thus, $pA_{Sp}A_{Sp}A$, which is a metabolically stable inhibitor of RNase L, has potential utility in treating myelogenous leukemia.

$pA_{Sp}A_{Sp}A$ is the most effective inhibitor of RNase L reported to date. Moreover, notwithstanding its RNase L inhibitory effect, $pA_{Sp}A_{Sp}A$ is observed to inhibit HIV reverse transcriptase activity and tobacco mosaic virus replication.

For pharmaceutical use, the compounds of the invention may be taken up in pharmaceutically acceptable carriers, such as, solutions, suspensions, tablets, capsules, ointments, elixirs and injectable composition and the like. They are administered to subjects suffering from viral infection. The dosage administered depends upon the nature and severity of the infection, the disease stage, and, when administered systematically, the size and weight of the infected subject.

The compounds are generally administered in the form of water-soluble salts. Pharmaceutically acceptable water soluble salts include, for example, the sodium, potassium or ammonium salts of the active compounds. They are readily dissolved in water or saline solution. Thus, the preferred formulation for pharmacological use comprises a saline solution of the desired compound in salt form. The formulation may further contain an agent, such as a sugar or protein, to maintain osmotic balance. The salt form of the compound is preferred owing to the relatively high acidity (about pH 3) of the acid form of the compounds.

The compounds of the invention may be used to treat or protect humans and animals from vital infectives such as Herpes simplex, rhinovirus, Epstein Barr virus, measles virus, multiple sclerosis (which may be caused by a viral agent) and the various Human Immunodeficiency Viruses ("HIV") such as HIV-1, which causes cutaneous T cell lymphoma, HIV-2, which causes Sezary lymphoma, and HIV-3, which is responsible for acquired immune deficiency syndrome ("AIDS"). The compounds of the invention inhibit the reverse transcriptase activity of HIV.

The compounds may be applied topically to treat skin cancers caused by radiation, carcinogens or viral agents. Such skin cancers include cutaneous T-cell lymphoma, Sezany lymphoma, Xeroderma pigmentosium, ataxia telangiectasia and Bloom's syndrome. A sufficient amount of a preparation containing a compound of the invention is applied to cover the lesion or affected area. An effective concentration of active agent is between about $10^{-3}$M and $10^{-5}$M, with $10^{-4}$ M being preferred.

Effect of 2',5'-Phosphorothioate Oligoadenylates on HIV Reverse Transcriptase Activity HIV reverse transcriptase (RNA-dependent DNA nucleotidyl-transferase) activity was assayed by a modification of the procedure of Poiesz et al. (Poiesz, B. J., Ruscetti , F. W., Gazdar, A. F., Bunn, P. S., Minna, J. D., and Gallo, R. C., *Proc. Natl. Acad. Sci. U.S.A.* 77: 7415–7419 (1980)).

Cultured H-9 cells are grown at 106 cells/ml in RPMI-1640 medium and 20% heat-inactivated fetal calf serum. Cell suspensions are centrifuged (1000×g, 10 min.) and the supernatant is removed. Virus particles are precipitated from this cell-free supernatant to which 0.3 ml of 4M NaCl and 3.6 ml of 30% (weight/volume) polyethylene glycol are added. The suspension is placed on ice for 2 hr following centrifugation at 15,000×g for 30 min at 0° C. The precipitate is resuspended in 200 microliters of 50% glycerol (vol./vol.)/25 mM Tris-HCl (pH 7.5)/5 mM dithiothreitol/50 mM KCl/0.025% Triton X-100. Virus particles are lysed by the addition of 100 microliters of 0.9% Triton X-100/1.5M KCl. Reverse transcriptase assays are performed at 37° C. for 1 hr with 10 microliters of the lysed virus solution in a final reaction volume of 100 microliters containing: 40 mM Tris-HCl (pH 7.8), 4 mM dithiothreitol, 45 mM KCl and 2.5 micrograms of template primer [poly(A)-dT$_{15}$, 0.5 micrograms/microliter] (with a signal Mg$^{++}$ concentration of 10 mM). At this time, 10 microliters of the 2',5'-phosphorothioate oligoadenylate is added to a final concentration of 200 micromolar. Reaction mixtures also contain 4 micromoles of [$^3$H]dTTP. Reactions are stopped by the addition of cold 5% trichloroacetic acid and filtered through nitrocellulose discs.

The discs are dried and the radioactivity bound to the discs is determined. Reverse transcriptase activity is expressed as the percent relative to a control.

The data is shown in Table 5. The compounds were assayed in the above manner in two sets, each set having a separate set of controls. The compounds of reactions 1–4 were assayed against control #1, which was $187 \times 10^3$ cpm. The compounds used in reactions 5–13 were assayed against control #2, which was $273 \times 10^3$ cpm.

TABLE 5

Inhibition of HIV (HTLV-III$_{BH-9}$) Reverse Transcriptase Activity by 2',5'-Phosphorothioate Oligoadenylates

| Reaction No. | Compound | Concentration (uM) | Reverse Transcriptase Activity (cpm × 10$^{-3}$) | Percent Inhibition |
|---|---|---|---|---|
| 1 | p$_3$A$_3$ | 200 | 187 | 0 |
| 2 | pA$_3$ | 200 | 133 | 29 |
| 3 | A$_3$ | 200 | 201 | 0 |
| 4 | pA$_{Rp}$A$_{Rp}$A | 200 | 144 | 25 |
| 5 | pA$_{Sp}$A$_{Rp}$A | 200 | 230 | 16 |
| 6 | pA$_{Rp}$A$_{Sp}$A | 200 | 206 | 25 |
| 7 | pA$_{Sp}$A$_{Sp}$A | 200 | 232 | 15 |
| 8 | A$_{Rp}$A$_{Rp}$A | 200 | 224 | 18 |
| 9 | A$_{Sp}$A$_{Rp}$A | 200 | 258 | 6 |
| 10 | A$_{Rp}$A$_{Sp}$A | 200 | 247 | 10 |
| 11 | A$_{Sp}$A$_{Sp}$A | 200 | 219 | 20 |
| 12 | A$_{Sp}$A$_{Sp}$A$_{Sp}$A | 200 | 149 | 45 |
| 13 | A$_{Rp}$A$_{Sp}$A$_{Sp}$A | 200 | 147 | 46 |

Although p$_3$A$_3$, pA$_3$ and A$_3$ are found in mammalian cells, only the monophosphate inhibits HIV reverse transcriptase. The core compounds of the present invention on the other hand are observed to inhibit HIV reverse transcriptase. While all the compounds of the invention (reaction nos. 5,6,7,9,10,11,12 and 13) inhibit the transcriptase to some degree, the tetramers are particularly effective.

The compounds of the invention may be administered in amounts of from about 10 micromoles to about 200 micromoles to inhibit HIV reverse transcriptase and treat HIV.

The compounds also possess antiviral activity against plant-infecting virus, particularly tobacco mosaic virus. Similar results may be obtained against other viruses which cause necrosis in turnips, cucumber, orchids and in other plants. Such viruses include, but are not limited to, tobacco vein mottling virus, vesicular stomatitis virus, vaccinia virus, turnip necrosis virus, and cymbidium orchid virus.

The compounds may be administered effectively to plants by topical application by abrasion of the leaf surface, aerosol spray, treatment of the soil, spraying, or dusting.

An effective antiviral composition may be formed by combining one or more of the compounds of the invention with a suitable carrier material. While the individual stereoisomers are preferred for pharmaceutical use, mixtures of one or more of stereoisomers may be employed in agricultural applications. The active compound may also be administered by spraying insect vectors such as aphids, thrips and whiteflies which carry virus to plants. The dosage administered depends upon the severity of the infection.

The compounds of the invention may be applied to plant seeds prior to germination to control viruses contained in the germ plasm. The seeds may be soaked in a solution of polyethylene glycol ("PEG") containing one or more of the compounds. PEG brings the seeds to physiological activity and arrest. The relative concentration of active compound to PEG depends upon the type of seed under treatment.

Plants are effectively treated with an aqueous formulation containing from about $10^{-1}$ to about $10^{-2}$M concentration of active ingredient. The compounds of the invention may be applied at very low concentrations. An effective amount of active ingredient on the plant surface is from about $10^{-8}$ to about $10^{-12}$ mole per cm$^2$ of plant surface area, with about $10^{-10}$ mole to about $10^{-12}$ mole per cm$^2$ being preferred. For the typical tobacco plant of 1000 cm$^2$, $10^{-5}$M of compound is effective. At this rate, one pound of active ingredient is sufficient to treat $2 \times 10^8$ tobacco plants.

For agricultural application, the compounds are advantageously administered in the form of water-soluble salts, e.g. ammonium or potassium salts. Sodium salts are generally avoided in treating edible plants.

The compounds of the invention are readily dissolved in water, particularly at such low concentrations. Aqueous formulations for agricultural use may optionally contain a sticker and/or a UV-stabilizer. Such agents are well-known to those skilled in the art. Fatty acids (1%) are useful as spreader sticker agents. Effective UV-stabilizers include, for example, p-aminobenzoic acid.

Effect of 2',5'-Phosphorothioate Oligoadenylates on Tobacco Mosaic Virus (TMV) Replication in Intact Tobacco Plants The effectiveness of the 2',5'-phosphorothioate oligoadenylates against plant virus was demonstrated by infectivity tests on intact *Nicotiana glutinosa* plants as follows.

Carborundum (400 mesh) was sprinkled lightly onto leaves. Solutions containing 0.2 micrograms per ml of TMV and $2 \times 10^{-5}$M 2',5'-phosphorothioate oligoadenylate in phosphate buffer were applied onto half-leaves of *N. glutinosa* with either a gloved finger or with a pipettor. The remaining half-leaves were controls (inoculated with the buffer solution containing TMV, but no active compound). The infection was allowed to proceed 48 h under continuous illumination of about 1500 Lx at which time local virus lesions appeared. Inhibition of TMV replication was calculated as the percent of local lesions produced in 2',5'-phosphorothioate oligoadenylate-treated half-leaves compared to control half-leaves. The data is set forth in Table 6.

TABLE 6

| Compound[3] | Percent TMV Inhibition[4] |
|---|---|
| — | 0 |
| A$_3$ | 16 |
| A$_{Rp}$A$_{Rp}$A | 57 |
| A$_{Sp}$A$_{Sp}$A | 80 |
| A$_{Rp}$A$_{Sp}$A | 70 |
| A$_{Sp}$A$_{Rp}$A | 33 |
| pA$_{Rp}$A$_{Rp}$A | 75 |
| pA$_{Rp}$A$_{Sp}$A | 15 |
| pA$_{Sp}$A$_{Rp}$A | 23 |
| pA$_{Sp}$A$_{Sp}$A | 40 |
| A$_{Sp}$A$_{Sp}$A$_{Sp}$A | 70 |
| A$_{Rp}$A$_{Sp}$A$_{Sp}$A | 80 |

[3]All compounds were added at $2 \times 10^{-5}$ M in the infecting solution.
[4]Inhibition of TMV replication was detected 48 hr after infection and was calculated as the percent of local lesions produced in treated half-leaves of *N. glutinosa* compared to control half-leaves.

Non-infected plants were treated with $2 \times 10^{-6}$M and $2 \times 10^{-5}$M of the 2',5'-phosphorothioate core and 5'-monophosphate analogues. No toxicity (chlorosis or necrosis) was observed during the two week period tested.

Of the ten phosphorothioate trimer and tetramer cores and 5'-monophosphates tested, the SpSp phosphorothioate trimer core inhibited TMV replication to the greatest extent (80%). Similarly, the corresponding tetramer core, SpSpSp, inhibited TMV replication by 70%. The RpSpSp tetramer core inhibited TMV replication by 80%. The remarkable inhibition by $A_{Sp}A_{Sp}A$, $A_{Sp}A_{Sp}A_{Sp}A$ and $A_{Rp}A_{Sp}A_{Sp}A$, as well as the 70% inhibition by $A_{Rp}A_{Sp}A$, compares with only a 16% inhibition with authentic $A_3$. By introducing the property of chirality, as well as increased metabolic stability, there is a marked increase of the inhibition of TMV replication by the compounds of the invention over 2-5A.

In addition to administration with conventional carriers, the compounds of the present invention may be administered by a variety of specialized oligonucleotide or nucleic acid delivery techniques. 2-5A and its analogues have been successfully encapsulated in unilamellar liposomes and delivered with the aid of monoclonal antibodies to cells (Bayard et al, *Eur. J. Biochem.* 151:319–325 (1985)). Reconstituted Sendai virus envelopes have been successfully used to deliver RNA and DNA to cells (Arad et al, *Biochem. Biophys. Acta.* 859:88–94 (1986)). These techniques may be utilized for introduction of the present 2',5'-phosphorothioate oligoadenylates into cells.

It is further contemplated that the compounds of the invention may be administered in the form of prodrugs in which lipophilic groups are attached to, for example, the 5'-terminal hydroxyl group of the core compound.

Conjugation of 2',5'-Phosphorothioate Tetramer Adenylates

Poly(L-lysine) has been described as a versatile membrane carrier for 2-5A and other macromolecules (Bayard et al, *Biochem.* 25:3730–3726 (1986)). The tetramer cores and phosphorylated tetrarmers of the present invention may be conveniently administered in the form of poly(L-lysine) conjugates. The conjugates are formed by introducing two aldehyde functions at the 2' end of the tetramer by periodate oxidation of the alpha-glycol group of the ribose residue. The resulting aldehyde groups are then randomly coupled to the epsilon-amino groups of lysine residues of poly(L-lysine) by Schiff base formation, and then reduced with sodium cyanoborohydride at pH 8.0. This procedure converts the 2',3'-terminal ribose ring into a morpholine structure. The poly(L-lysine) peptide preferably contains from about 60 to about 70 lysine residues. From about five to about ten of the lysine residues are coupled in this manner to tetramer moieties. The resulting 2',5'-phosphorothioate/poly(L-lysine) conjugates may then be isolated by gel filtration chromatography on a Sephadex G-50 column.

The poly(L-lysine)/2',5'-phosphorothioate ologoadenylate conjugates have the formula:

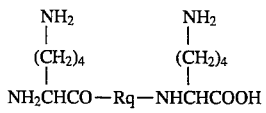

wherein q is an integer from about 60 to about 70 and R is randomly R' or

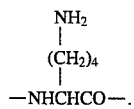

From about five to about ten of the R groups comprise R'. The R' group has the following formula wherein m is 0,1,2 or 3:

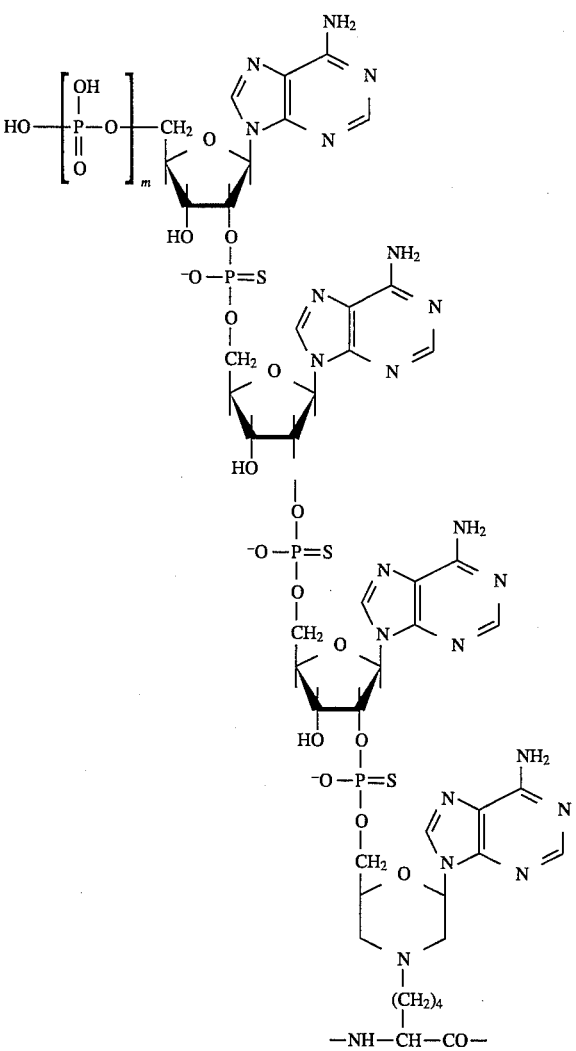

The conjugates may be advantageously prepared by the procedure of Bayard et al, *Biochem.* 25:3730–3736 (1986):

Example 18

Preparation of Poly(L-lysine)/2',5'-Phosphorothioate Oligoadenylate Conjugates A 4-microliter aliquot of sodium metaperiodate (0.6 micromole in 0.1M sodium acetate buffer, pH 4.75) is added to an ice-cold solution of 2',5'-phosphorothioate tetramer adenylate in 400 microliter of distiller water. The reaction mixture is stirred on ice for 30 min; 400 microliter of poly(L-lysine) (0.14 micromole in 0.2M phosphate buffer, pH 8.0) and 200 microliter of sodium cyanoborohydride (20 micromole in 0.2M phosphate buffer, pH 8.0) are added. The mixture is incubated for 2 h at room temperature and then loaded on a Sephadex G-50 column equilibrated with 0.1M sodium acetate buffer, pH 4.75. Each fraction is assayed for its phosphorothioate oligoadenylate/poly(L-lysine) content by the method described by Lowry et al, *J. Biol. Chem.* 193:265–275 (1951), and by absorbance at 260 nm.

Conjugation of the 2',5'-phosphothioate tetramer to poly(L-lysine) leaves the remaining three 2',5'-linked phosphorothioate adenylic residues intact for optimal RNase L binding and activation.

Liposome Encapsulation of 2',5'-Phosphorothioate Oligoadenylates

Encapsulation of the compounds of the present invention comprises another attractive non-disruptive technique for introduction into cells. Liposome encapsulation may be advantageously accomplished according to the technique described by Kondorosi et al., *FEBS Lett.* 120:37–40 (1980):

EXAMPLE 19

Preparation of Large Unilamellar Vesicles (Liposomes) Loaded with 2',5'-Phosphorothioate Oligoadenylates Briefly, a phospholipid mixture from bovine brain (Sigma Chemical Co., Folch fraction III composed of 80–85% phosphatidylserine with the remaining 15% composed of other brain lipids; 35 mg) is suspended in 5 ml of buffer A [0.1M NaCl, 2 mM histidine, 2 mM N-tris(hydroxymethyl) methyl-2-aminoethane sulfonic acid ("TES"), 0.4 mM EDTA (pH 7.4) by vortexing. The suspension is sonicated under nitrogen for 10 minutes at 0° C. The suspension is further incubated for 1 hr at 37° C. after adjusting the final concentration of $Ca^{++}$ to 20 mM by the addition of 125 microliters of 800 mM $CaCl_2$. The resulting precipitate is sedimented by centrifugation (2500×g, 10 min), vortexing and mixing with 100 microliters of $1\times10^{-4}M$ 2',5'-phosphorothioate oligoadenylate, which is dissolved in phosphate-buffered saline. The final concentration of EDTA is then adjusted to 120 mM by the addition of 400 microliters of buffer B [150 mM EDTA, pH 7.4, 0.1M NaCl, 2 mM histidine, 2 mM TES]. Liposomes are formed after incubation of this mixture for 30 minutes at 37° C. The excess of EDTA and non-encapsulated components are removed by passing the liposomes through a Sephadex G-25 column which is equilibrated with phosphate-buffered saline. About 10% of the 2',5'-phosphorothioate oligoadenylate is encapsulated into liposomes by this procedure. The liposome suspension is stable at 4° C. for one week following preparation.

Preparation of Reconstituted Sendai Virus Envelopes Containing 2',5'-Phosphorothioate Oligoadenylates Reconstituted Sendai virus envelopes may be used as efficient vehicles for the introduction of polynucleotides into cells. Arad et al, *Biochimica et Biophysica Acta* 859:88–94 (1986) disclose introduction of poly(I).poly(C) into cultured cells by the use of reconstituted Sendai virus envelopes. Fusion of thus-loaded reconstituted Sendai virus envelopes leads to introduction of the enclosed macromolecules into the recipient cell cytoplasm.

Reconstituted Sendai virus envelopes may be obtained by detergent solubilization of intact Sendai virus particles. The reconstituted envelopes are fusogenic vesicles consisting of the vital envelope phospholids and their glycoproteins, devoid of the viral genomic RNA.

Incorporation of the compounds of the present invention into reconstituted Sendai virus envelopes for fusion-mediated micro-injection may be accomplished by following the procedure or Arad et al. Briefly, a pellet of Sendai virus particles (1.5 mg protein) is dissolved in 30 microliters of a solution containing 10% Triton X-100, 100 mM NaCl, 50 mM Tris-HCl (pH 7.4) and 0.1 mM phenylmethylsulfonyl fluoride (Triton X-100:protein ratio, 2:1, w/w). To the clear supernatant obtained after centrifugation, 2',5'-phosphorothioate oligoadenylate dissolved in a solution A (160 mM NaCl, 20 mM Tris-HCl, (pH 7.4)) is added to give a final concentration of active ingredient of 5–20 mg/ml and a final volume of 150 microliters. Triton X-100 is removed from the supernatant by direct addition of 40 mg of SM-2 Bio-Beads. The turbid suspension obtained (containing reconstituted Sendai virus envelopes) is centrifuged at 100,000×g for 1 h. The pellet, containing about 10% of the original viral protein, is then suspended in solution A to give a final protein concentration of 25 micrograms/ml.

The present invention may be embodied in other specific forms without departing from the spirit or essential attributes thereof and, accordingly, reference should be made to the appended claims, rather than to the foregoing specification, as indicating the scope of the invention.

We claim:

1. A method for treating viral infection in mammals comprising administering thereto an antiviral effective amount of a compound which is an optical isomer of the formula:

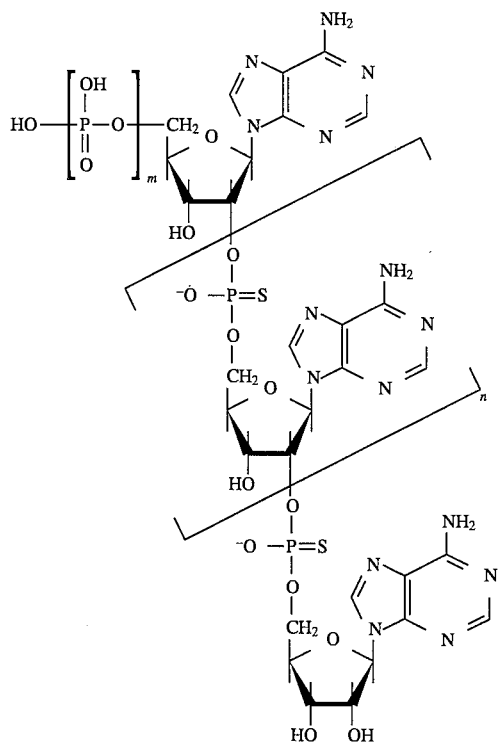

substantially free of contamination by other optical isomers of the same formula, where m is zero, 1, 2, or 3; n is 1 or 2; and at least one of the internucleotide phosphorothioate groups

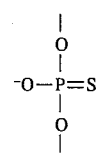

is of the Sp configuration; or water-soluble salt thereof.

2. A method according to claim 1 wherein m is 1.

3. A method according to claim 1 for treatment of viral infection in a human being.

4. A method according to claim 3 for inhibiting human immunodeficiency virus infection.

5. A method according to claim 1 wherein the compound is (Sp)-P-thiadenylyl-(2'-5')-(Rp)-P- thiadenylyl-(2'-5')-adenosine, the 5'-monophosphate thereof, or water-soluble salt of said compound or said 5'-monophosphate.

6. A method according to claim 1 wherein the internucleotide phosphorotioate group adjacent the 2'-terminal adenylate moiety is of the Sp configuration.

7. A method according to claim 6 wherein the compound is (Rp)-P-thioadenylyl-(2'-5')-(Sp)-P- thioadenylyl-(2'-5')-adenosine, the 5'-monophosphate thereof, or water-soluble salt of said compound or said 5'-monophosphate.

8. A method according to claim 6 wherein the compound is (Sp)-P-thioadenylyl-(2'-5')-(Sp)-P- thioadenylyl-(2'-5')-adenosine, the 5'-monophosphate thereof, or water-soluble salt of said compound or said 5'-monophosphate.

9. A method according to claim 6 wherein the compound is (Rp)-P-thioadenylyl-(2'-5')-(Sp)-P-thioadenylyl-(2'-5')-(Sp)-P- thioadenylyl-(2'-5')-adenosine, the 5'-monophosphate thereof, or water-soluble salt of said compound or said 5'-monophosphate.

10. A method according to claim 6 wherein the compound is (Sp)-P-thioadenylyl-(2'-5')-(Sp)-P-thioadenylyl-(2'-5')-Sp)-P-thioadenylyl-( 2'-5')-adenosine, the 5'-monophosphate thereof, or water-soluble salt of said compound or 5'-monophosphate.

11. A method of inhibiting viral infection in plants comprising administering thereto an antiviral effective amount of a mixture of two or more optical isomers of a compound of the following formula

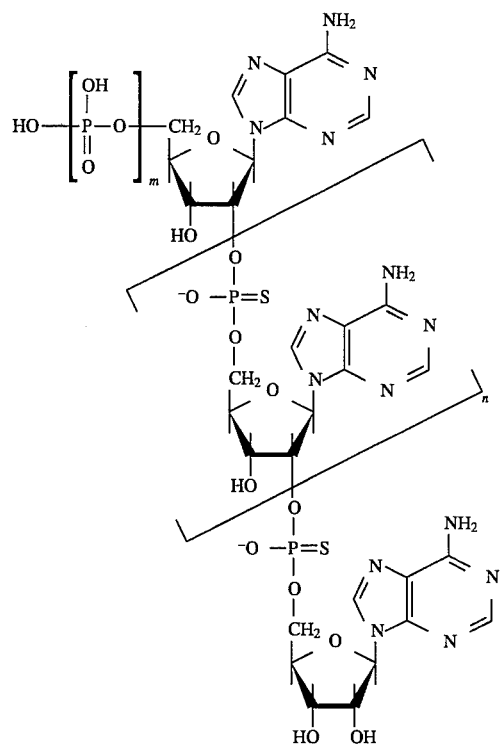

wherein m is zero, 1, 2, or 3 and n is 1 or 2, and water-soluble salts thereof.

12. A method according to claim 11 for inhibiting tobacco mosaic virus infection.

* * * * *